(12) United States Patent
Wiedenhoefer et al.

(10) Patent No.: US 11,684,260 B2
(45) Date of Patent: Jun. 27, 2023

(54) SYSTEM AND METHODS WITH USER INTERFACES FOR MONITORING PHYSICAL THERAPY AND REHABILITATION

(71) Applicant: Consensus Orthopedics, Inc., El Dorado Hills, CA (US)

(72) Inventors: Curt Wiedenhoefer, Davis, CA (US); Justin Anthony Creel, Fair Oaks, CA (US); Brian James Katerberg, Folsom, CA (US); Joshua Dale Howard, Sacramento, CA (US)

(73) Assignee: TRACPATCH HEALTH, INC., Sacramento, CA (US)

( * ) Notice: Subject to any disclaimer, the term of this patent is extended or adjusted under 35 U.S.C. 154(b) by 484 days.

(21) Appl. No.: 15/422,320

(22) Filed: Feb. 1, 2017

(65) Prior Publication Data
US 2017/0147789 A1 May 25, 2017

Related U.S. Application Data

(63) Continuation-in-part of application No. 15/077,809, filed on Mar. 22, 2016, now Pat. No. 10,709,377.
(Continued)

(51) Int. Cl.
*A61B 5/103* (2006.01)
*A61B 5/00* (2006.01)
(Continued)

(52) U.S. Cl.
CPC ............ *A61B 5/0031* (2013.01); *A61B 1/041* (2013.01); *A61B 5/02055* (2013.01);
(Continued)

(58) Field of Classification Search
CPC ..... A61B 5/0022; A61B 5/6804; A61B 5/743; G16H 40/67
See application file for complete search history.

(56) References Cited

U.S. PATENT DOCUMENTS

| 3,724,651 A | 4/1973 | Link |
| 4,353,135 A | 10/1982 | Forte et al. |
| (Continued) | | |

FOREIGN PATENT DOCUMENTS

| CN | 201537084 | 8/2010 |
| CN | 102472719 | 5/2012 |
| (Continued) | | |

OTHER PUBLICATIONS

International Search Report and Written Opinion for PCT/US2018/016424 dated Mar. 28, 2018.
(Continued)

*Primary Examiner* — Michael J D'Abreu
(74) *Attorney, Agent, or Firm* — Branch Partners PLLC; Bruce E. Black

(57) ABSTRACT

A system for monitoring a joint of a patient includes multiple sensors to be disposed near a joint and to measure or observe actions or physical quantities associated with the joint; and at least one communications module coupled to the sensors to receive data from the sensors and to transmit sensor information to an external device. The system also includes a patient device and clinician device which can be used to, for example, monitor and display information obtained from the sensors, determine range of motion measurements from the sensor data, show progress in physical therapy, take a photograph or video of the site on the patient, obtain a pain score, and include friends for providing encouragement during physical therapy.

20 Claims, 14 Drawing Sheets

Related U.S. Application Data

(60) Provisional application No. 62/136,925, filed on Mar. 23, 2015, provisional application No. 62/136,892, filed on Mar. 23, 2015.

(51) Int. Cl.
| | |
|---|---|
| *G16H 50/30* | (2018.01) |
| *A61B 5/07* | (2006.01) |
| *A61B 5/0205* | (2006.01) |
| *A61B 1/04* | (2006.01) |
| *G16H 20/30* | (2018.01) |
| *G16H 40/67* | (2018.01) |
| *A61B 5/024* | (2006.01) |
| *A61B 90/30* | (2016.01) |
| *A61B 5/11* | (2006.01) |
| *A61B 5/107* | (2006.01) |

(52) U.S. Cl.
CPC .......... *A61B 5/076* (2013.01); *A61B 5/4528* (2013.01); *A61B 5/4851* (2013.01); *G16H 20/30* (2018.01); *G16H 40/67* (2018.01); *G16H 50/30* (2018.01); *A61B 5/0013* (2013.01); *A61B 5/024* (2013.01); *A61B 5/1071* (2013.01); *A61B 5/112* (2013.01); *A61B 5/1118* (2013.01); *A61B 5/1121* (2013.01); *A61B 5/4585* (2013.01); *A61B 5/6833* (2013.01); *A61B 5/743* (2013.01); *A61B 2090/309* (2016.02); *A61B 2505/09* (2013.01); *A61B 2560/0214* (2013.01); *A61B 2562/0219* (2013.01); *A61B 2562/0223* (2013.01); *A61B 2562/0247* (2013.01)

(56) References Cited

U.S. PATENT DOCUMENTS

| | | | |
|---|---|---|---|
| 4,756,312 A | 7/1988 | Epley | |
| 5,833,603 A | 11/1998 | Kovacs et al. | |
| 6,588,931 B2 | 7/2003 | Betzner et al. | |
| 8,784,274 B1 | 7/2014 | Chuang | |
| 8,990,041 B2 | 3/2015 | Grabiner et al. | |
| 9,138,174 B2 | 9/2015 | Jin et al. | |
| 9,176,932 B2 | 11/2015 | Baggen et al. | |
| 1,086,392 A1 | 12/2020 | Mobbs et al. | |
| 2003/0069714 A1 | 4/2003 | Wigley et al. | |
| 2003/0163287 A1 | 8/2003 | Vock et al. | |
| 2004/0039254 A1 | 2/2004 | Stivoric et al. | |
| 2004/0122334 A1 | 6/2004 | Yamashiro | |
| 2004/0167390 A1 | 8/2004 | Alexander et al. | |
| 2005/0010299 A1 | 1/2005 | Disilvestro | |
| 2005/0010301 A1 | 1/2005 | Disilvestro et al. | |
| 2005/0197540 A1 | 9/2005 | Liedtke | |
| 2007/0167688 A1* | 7/2007 | Ross ............... | G16H 10/20 600/300 |
| 2007/0250286 A1 | 10/2007 | Duncan et al. | |
| 2008/0027296 A1 | 1/2008 | Hadvary et al. | |
| 2008/0299960 A1* | 12/2008 | Lockhart ........... | H04L 51/00 455/418 |
| 2008/0311765 A1 | 12/2008 | Chatterjee et al. | |
| 2009/0309683 A1 | 12/2009 | Cochran | |
| 2010/0114596 A1* | 5/2010 | Williams ........... | G06Q 10/10 705/2 |
| 2010/0174189 A1 | 7/2010 | Abraham | |
| 2010/0228089 A1 | 9/2010 | Hoffman et al. | |
| 2010/0262047 A1* | 10/2010 | Genis ............... | A61B 5/1124 601/5 |
| 2010/0324403 A1 | 12/2010 | Brister et al. | |
| 2011/0046558 A1 | 2/2011 | Gravesen et al. | |
| 2011/0208444 A1 | 8/2011 | Solinsky | |
| 2011/0213275 A1 | 9/2011 | Boos et al. | |
| 2011/0231208 A1* | 9/2011 | Kaplin ............. | G16H 40/67 705/3 |
| 2011/0245711 A1 | 10/2011 | Katra et al. | |
| 2011/0288379 A1 | 11/2011 | Wu | |
| 2012/0143135 A1 | 6/2012 | Cole et al. | |
| 2013/0211259 A1 | 8/2013 | Komistek et al. | |
| 2013/0217998 A1 | 8/2013 | Mahfouz et al. | |
| 2014/0015687 A1 | 1/2014 | Narasimhan et al. | |
| 2014/0049911 A1 | 2/2014 | Corbin et al. | |
| 2014/0100464 A1* | 4/2014 | Kaleal ............. | A61B 5/0205 600/508 |
| 2014/0114453 A1 | 4/2014 | Bentley | |
| 2014/0128778 A1 | 5/2014 | Chan et al. | |
| 2014/0142864 A1 | 5/2014 | Spears et al. | |
| 2014/0157911 A1* | 6/2014 | Sarrafzadeh ......... | A61B 5/1036 73/862.041 |
| 2014/0274413 A1* | 9/2014 | Chelst ............... | A63F 13/847 463/42 |
| 2014/0275815 A1 | 9/2014 | Stein et al. | |
| 2014/0316526 A1 | 10/2014 | Grotz | |
| 2014/0358193 A1 | 12/2014 | Lyons et al. | |
| 2015/0003699 A1 | 1/2015 | Davis et al. | |
| 2015/0019135 A1 | 1/2015 | Kacyvenski et al. | |
| 2015/0045700 A1 | 2/2015 | Cavanagh et al. | |
| 2015/0230183 A1 | 8/2015 | Stogaitis et al. | |
| 2015/0238094 A1 | 8/2015 | Lai et al. | |
| 2015/0282796 A1 | 10/2015 | Nawana et al. | |
| 2015/0302162 A1* | 10/2015 | Hughes ............. | G09B 19/0038 702/19 |
| 2016/0007861 A1 | 1/2016 | Tseng et al. | |
| 2016/0066843 A1 | 3/2016 | Mensinger et al. | |
| 2016/0077596 A1 | 3/2016 | Pantelopoulos et al. | |
| 2016/0220176 A1 | 8/2016 | Desnerck et al. | |
| 2016/0302674 A1 | 10/2016 | Moyer et al. | |
| 2016/0302721 A1 | 10/2016 | Wiedenhoefer et al. | |
| 2016/0310066 A1 | 10/2016 | Wiedenhoefer et al. | |
| 2017/0143261 A1 | 5/2017 | Wiedenhoefer et al. | |
| 2017/0181698 A1 | 6/2017 | Wiedenhoefer et al. | |
| 2017/0241797 A1 | 8/2017 | Kong et al. | |
| 2017/0244827 A1 | 8/2017 | Kang et al. | |
| 2017/0273601 A1 | 9/2017 | Wang et al. | |
| 2018/0116572 A1 | 5/2018 | Simpson et al. | |
| 2018/0177436 A1 | 6/2018 | Chang et al. | |
| 2018/0199674 A1 | 7/2018 | Walker et al. | |
| 2019/0336825 A1 | 11/2019 | Douglas et al. | |

FOREIGN PATENT DOCUMENTS

| | | |
|---|---|---|
| CN | 104068831 | 10/2014 |
| EP | 1938749 | 7/2008 |
| JP | 2012090946 | 5/2012 |
| JP | 2012110573 | 6/2012 |
| JP | 2012-223452 | 11/2012 |
| JP | 2013013579 | 1/2013 |
| JP | 2014138661 | 7/2014 |
| JP | 2015062654 | 4/2015 |
| KR | 20160033828 | 3/2016 |
| WO | 94/26359 | 11/1994 |
| WO | 2008/120215 | 10/2008 |
| WO | 2010/088696 | 8/2010 |
| WO | 2013/072234 | 5/2013 |
| WO | 2015/127218 | 8/2015 |
| WO | 2016/191753 | 8/2015 |
| WO | 2016/029138 | 2/2016 |

OTHER PUBLICATIONS

International Search Report and Wiillen Opinion for PCT/US2018/016417 dated Mar. 29, 2018.
International Search Report and Written Opinion for PCT/US2018/016422 dated Apr. 16, 2018.
Official Communication for U.S. Appl. No. 15/077,809 dated Dec. 28, 2017.
Official Communication for U.S. Appl. No. 15/422,299 dated Apr. 4, 2018.
Official Communication for U.S. Appl. No. 15/077,809 dated Jul. 2, 2019.
Official Communication for U.S. Appl. No. 15/077,809 dated Nov. 2, 2018.

(56) References Cited

OTHER PUBLICATIONS

Official Communication for U.S. Appl. No. 15/077,793 dated Jul. 15, 2019.
Official Communication for U.S. Appl. No. 15/077,793 dated Mar. 21, 2019.
Official Communication for U.S. Appl. No. 15/077,793 dated Oct. 25, 2018.
Official Communication for U.S. Appl. No. 15/422,299 dated May 2, 2019.
International Search Report and Written Opinion for PCT/US2016/023637 dated Aug. 9, 2016.
International Search Report and Written Opinion for PCT/US2016/023632 dated May 31, 2016.
Martinson et al., "Implementation of motion capture support in smartphones," Department of Computer Science and Engineering, Chalmers University of Technology, Jan. 1, 2010, Retrieved from the Internet at http://studentarbeten.chalmers.se/publication/129442-implementation-of-motion-capture-support-in-smartphones.
U.S. Appl. No. 15/422,299, Entitled: System and Methods for Monitoring Physical Therapy and Rehabilitation of Joints, Inventor: Wiedenhoefer et al., filed Feb. 1, 2017.
U.S. Appl. No. 15/422,312, Entitled: Systems and Methods Using a Wearable Device for Monitoring an Orthopedic Implant and Rehabilitation, Inventor: Wiedenhoefer et al., filed Feb. 1, 2017.
Official Communication for U.S. Appl. No. 15/077,809 dated Dec. 11, 2019.
Official Communication for U.S. Appl. No. 15/077,793 dated Nov. 6, 2019.
Official Communication for U.S. Appl. No. 15/422,312 dated Nov. 15, 2019.
Official Communication for U.S. Appl. No. 15/422,312 dated May 1, 2020.
Nejati Hossein et al: "Smartphone and Mobile Image Processing for Assisted Living: Health-monitoring apps powered by advanced mobile imaging algorithms". IEEE Signal Processing Magazine. IEEE Service Center. Piscataway. NJ. US. vol. 33. No. 4. Jul. 1, 2016 (Jul. 1, 2016). pp. 30-48.
Rehamm Abo Elrahim et al: II Inter-rater and intra-rater reliability of Kinovea software for measurement of shoulder range of motion. Bulletin of Faculty of Physical Therapy, vol. 21. No. 2. Jan. 1, 2016 (Jan. 1, 2016). p. 80.
Giorgio Ferriero et al: "Reliability of a smartphone-based goniometer for knee joint goniometry :", International Journal of Rehabilitation Research, vol. 36, No. 2, Jun. 1, 2013 (Jun. 1, 2013), pp. 146-151.
Jorleeds Medical: "Orthophysical App—Gyroscope Test", Nov. 29, 2016 (Nov. 29, 2016), pp. 1-3, XP054980919, Retrieved from the Internet: URL:https://www.youtube.com/watch?v=buUqo9E35Mk [retrieved on Sep. 29, 2020].
Lenaerts B et al: "An Omnidirectional Transcutaneous Power Link for Capsule Endoscopy", Wearable and Implantable Body Sensor Networks, 2006. BSN 2006. International Workshop On Cambridge, MA, USA Apr. 3-5, 2006, Piscataway, NJ, USA, IEEE, Apr. 3, 2006 (Apr. 3, 2006), pp. 46-49.
Official Communication for U.S. Appl. No. 15/422,312 dated Dec. 9, 2020.
International Search Report and Written Opinion for PCT Application No. PCT/US2021/015520 dated Mar. 26, 2021.
Official Communication for U.S. Appl. No. 16/775,026 dated Mar. 6, 2020.
"Emerging technologies—An imaging pill for gastrointestinal endoscopy", IEEE Engineering in Medicine and Biology Magazine, IEEE Service Center, Piscataway, NJ, US, vol. 24, No. 4, Jul. 1, 2005 (Jul. 1, 2005), pp. 12-14.
Extended European Search Report for European Patent Application No. 18748777.2 dated Jul. 31, 2020.
Official Communication for U.S. Appl. No. 15/077,793 dated Nov. 29, 2021.
Official Communication for U.S. Appl. No. 16/813,548 dated Mar. 30, 2022.
Official Communication for U.S. Appl. No. 15/077,793 dated Aug. 24, 2022.
Official Communication for U.S. Appl. No. 16/927,561 dated Aug. 18, 2022.
Official Communication for U.S. Appl. No. 16/813,548 dated Oct. 20, 2022.

* cited by examiner

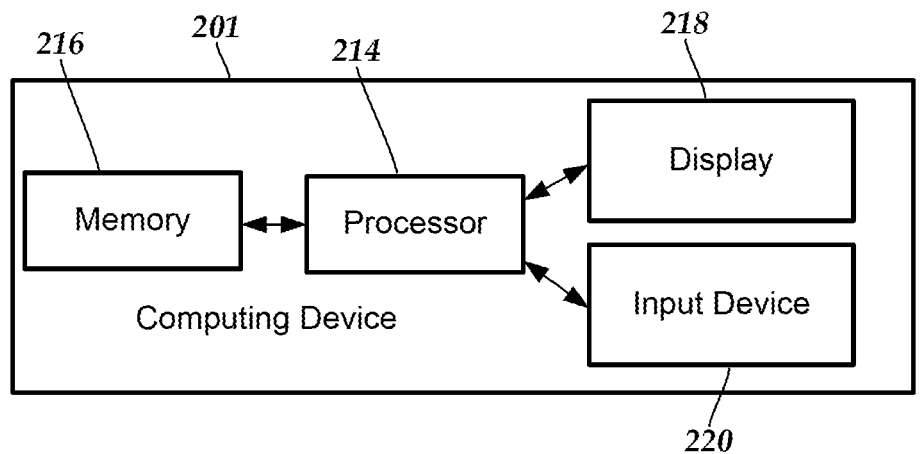
Fig. 2
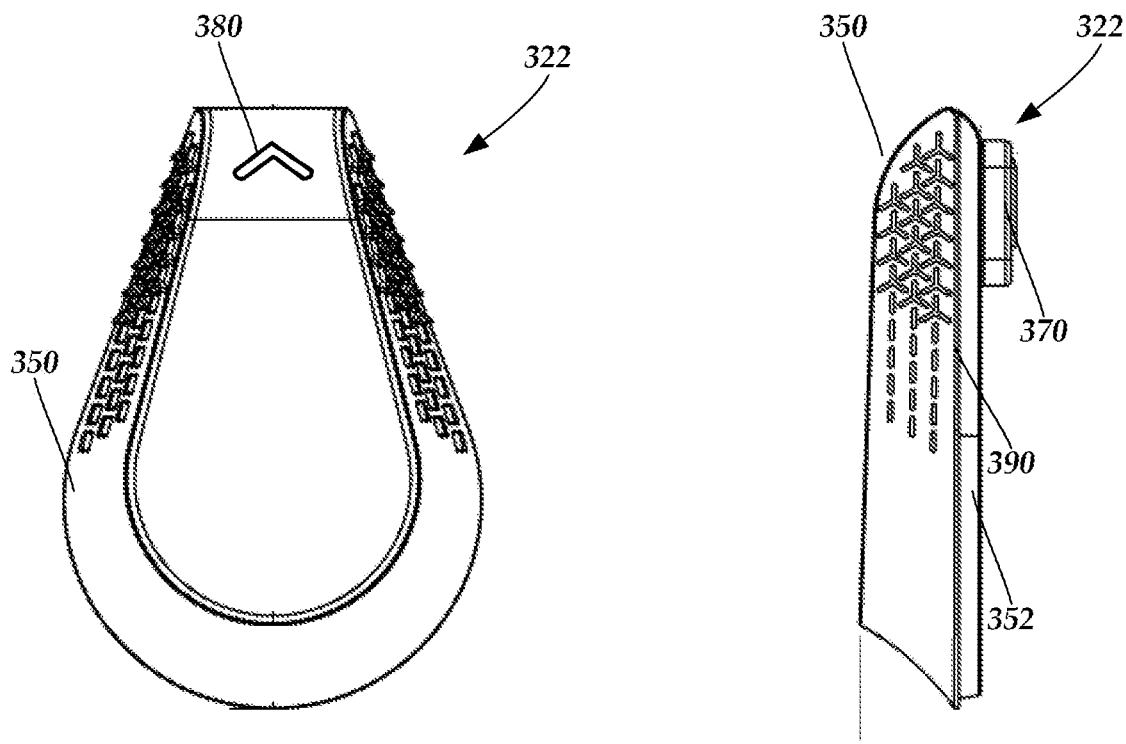
Fig. 4A
Fig. 4B

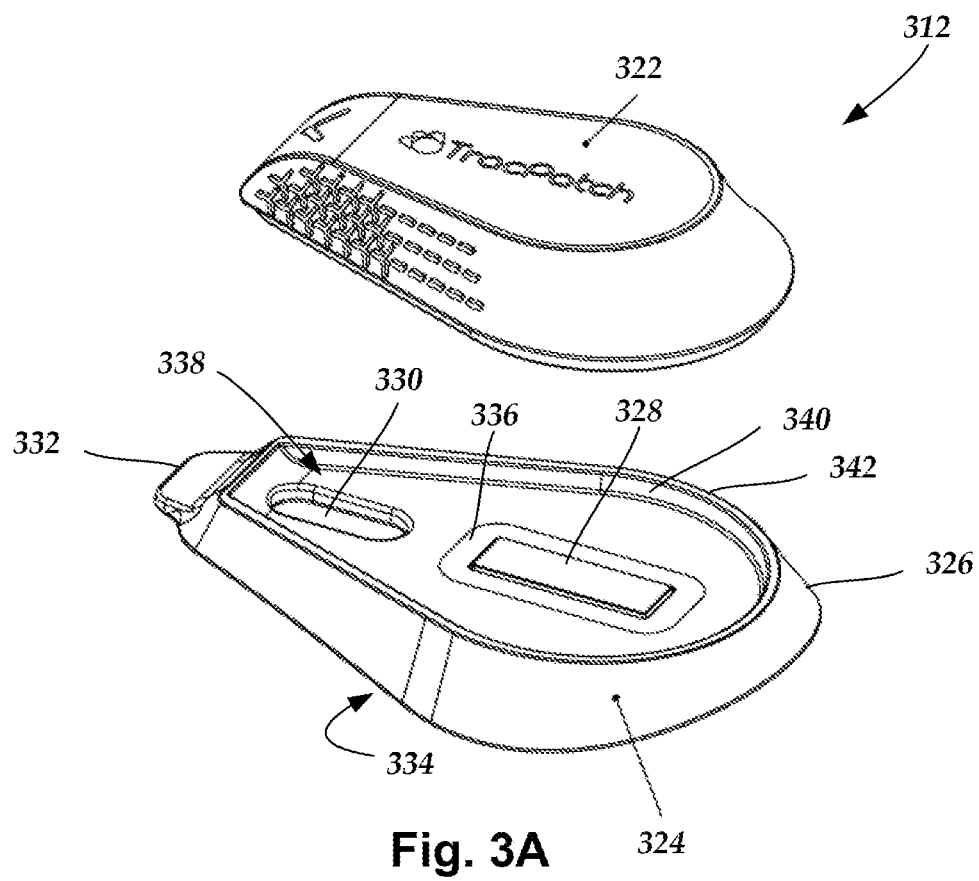
Fig. 3A
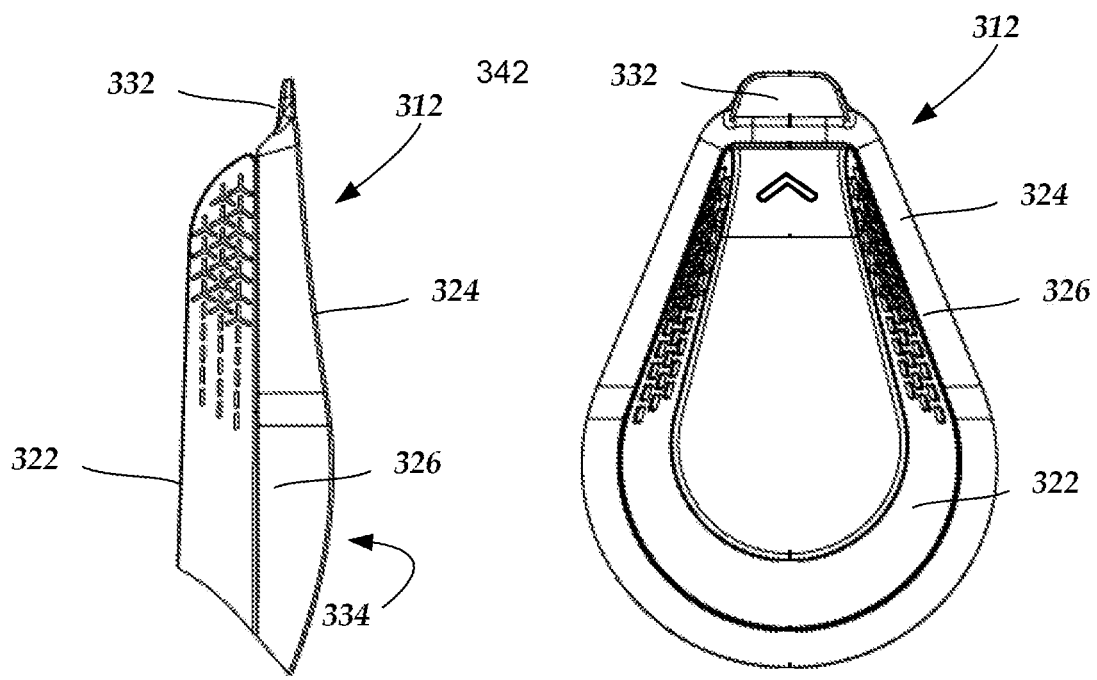
Fig. 3B
Fig. 3C

SYSTEM AND METHODS WITH USER INTERFACES FOR MONITORING PHYSICAL THERAPY AND REHABILITATION

CROSS-REFERENCE TO RELATED APPLICATIONS

This application is a continuation-in-part of U.S. patent application Ser. No. 15/077,809, filed Mar. 22, 2016, which claims the benefit of both U.S. Provisional Patent Application Ser. No. 62/136,892, filed Mar. 23, 2015, and U.S. Provisional Patent Application Ser. No. 62/136,925, filed Mar. 23, 2015, all of which are incorporated herein by reference in their entirety.

FIELD

The present invention is directed to the area of methods, systems, and devices, including user interfaces, for monitoring physical therapy or rehabilitation. The present invention is also directed to systems and methods with user interfaces for monitoring physical therapy or rehabilitation after surgery or implantation of an orthopedic device.

BACKGROUND

Joint replacement surgery is a common orthopedic procedure for joints such as the shoulder, hip, knee, ankle, and wrist. In situations where the patient has worn-out or damaged a joint, it is possible to replace the joint with an implant that can merge with the skeletal structure and restore pain free movement and function. Prior to implanting prosthetic components in a joint of a patient, a surgeon generally resects at least a portion of the patient's native bone in order to create a platform, recess, or cavity for receiving at least a portion of the prosthetic components being implanted. During the process of implanting the prosthetic components muscles and tendons must be repositioned and reattached.

The patient must go through physical therapy in order to recover from this major surgery. The patient must exercise regularly as well as push for flexibility and balance in muscles that have been displaced. While the goal is to have the patient extend their range of motion, there can be an increased risk of falls or over-extension that can damage the implant and injure the patient. If the patient does not push their rehabilitation and achieve the needed range of motion, they will find themselves with a stiff joint which may require an additional surgical operation (MUA—Manipulation Under Anesthesia) to achieve an adequate range of motion to maintain their active lifestyle. Measuring or monitoring the progress of the physical therapy can be problematic but is very useful for maintaining the patient's dedication and participation.

BRIEF SUMMARY

One embodiment is a system for monitoring a patient. The system includes a patient device configured and arranged for communication with a sensor unit disposed on or within the patient, the patient device including a display, a camera, a memory, and a processor coupled to the display, camera, and memory, wherein the processor is configured and arranged for performing actions including: directing, on the display, a user to take a photograph or video of a site on the patient; upon receiving a user-input to take the photograph or video, taking the photograph or video; and storing the photograph or video in memory.

In at least some embodiments, the actions further include performing a pigment analysis using the photograph or video to assess health of the site on the patient. In at least some embodiments, the actions further include, when the pigment analysis indicates possible infection of the site on the patient, producing a visual or audible warning to the patient. In at least some embodiments, the actions further include, when the pigment analysis indicates possible infection of the site on the patient, sending a message to a clinician device with an indication of the possible infection.

In at least some embodiments, the actions further include sending the photograph or video to a clinician device for assessment of health of the site on the patient. In at least some embodiments, the photograph or video is a video and the actions further include assessing performance of an exercise using the video. In at least some embodiments, the actions further include overlaying one or more lines or angles on the photograph or video to represent position or movement of a limb of the patient within the photograph or video.

Another embodiment is a system for monitoring a patient. The system includes a patient device configured and arranged for communication with a sensor unit disposed on or within the patient, the patient device including a display, a memory, and a processor coupled to the display, and memory, wherein the processor is configured and arranged for performing actions including: directing, on the display, a user to input a pain score; and sending the pain score to a clinician device.

In at least some embodiments, the actions further include receiving a selection by the user of an exercise; displaying, on the display, a graphical representation of the exercise and a user control which, when actuated by the user, indicates that the user is performing the exercise; and, upon actuation of the user control, monitoring sensor data from the sensor unit to monitor performance of the exercise. In at least some embodiments, the actions further include, during performance of the exercise, display a count of repetitions of the exercise being performed. In at least some embodiments, the actions further include, during performance of the exercise, display either a current value or a maximum achieved value of a range of motion measurement associated with the exercise, as determined from the sensor data.

In at least some embodiments, the actions further include receiving from the user a request for an exercise summary; and displaying, on the display, a summary of a plurality of exercises indicating a number of repetitions performed for each exercise over a period of time. In at least some embodiments, the actions further include receiving from the user a request for a progress report for a range of motion measurement; and displaying, on the display, a graph of a plurality of values for the range of motion measurement obtained over a period of time. In at least some embodiments, the actions further include displaying, on the display, a representation of a pathway to a goal for the range of motion measurement with an indication of current progress of the patient toward that goal.

A further embodiment is a system for monitoring physical therapy of a patient. The system includes a patient device configured and arranged for communication with a sensor unit disposed on or within the patient, the patient device including a display, a memory, and a processor coupled to the display, and memory, wherein the processor is configured and arranged for performing actions including: directing, on the display, a user to input one or more friends; sending a connection message to each of the one or more friends; and receiving from at least one of the one or more friends a message encouraging the patient to continue the physical therapy.

In at least some embodiments, the actions further include, in response to user input, sending a message to at least one of the one or more friends. In at least some embodiments, the actions further include, in response to user input, sending a challenge to at least one of the one or more friends. In at least some embodiments, the actions further include sending a progress report to at least one of the one or more friends, wherein the progress report includes an indication of progress by the patient toward at least one physical therapy goal. In at least some embodiments, the actions further include sending a progress report to at least one of the one or more friends, wherein the progress report includes an indication of patient performance of at least one physical therapy exercise. In at least some embodiments, the progress report further includes an indication of performance of the at least one physical therapy exercise by at least one of the one or more friends.

Yet another embodiment is a method for performing the actions recited for any of the systems described above. A further embodiment is a non-transitory computer readable medium comprising instructions for performing the actions recited for any of the systems described above.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 2 is a schematic diagram of one embodiment of a computing device for use in the system of FIG. 1, according to the invention;

FIG. 3A is a perspective side view of one embodiment of a sensor unit and a base disengaged from each other, according to the invention;

FIG. 3B is a side view of the sensor unit and base of FIG. 3A engaged with each other, according to the invention;

FIG. 3C is a top view of the sensor unit and base of FIG. 3A engaged with each other, according to the invention;

FIG. 4A is a top view of one embodiment of the sensor unit of FIG. 3A, according to the invention;

FIG. 4B is a side view of the sensor unit of FIG. 4A, according to the invention;

FIG. 5 is a diagram of one embodiment of a user interface for a mobile device to display a profile for a patient or clinician, according to the invention;

DETAILED DESCRIPTION

The present invention is directed to the area of methods, systems, and devices, including user interfaces, for monitoring physical therapy or rehabilitation. The present invention is also directed to systems and methods with user interfaces for monitoring physical therapy or rehabilitation after surgery or implantation of an orthopedic device.

A system, as described herein, can be used to monitor physical therapy or the healing process or rehabilitation of the patient after surgery, as well as monitor or verify the extent of the patient's activity. The system includes one or more sensors that can communicate with a processor that can produce information, based on the sensor readings and data, that can facilitate the patient or another user, such as a clinician, doctor, physical therapist, nurse, care coordinator, or other appropriate person, monitoring the patient's activity, the status of an orthopedic implant or surrounding tissues, or the effects of rehabilitation or other therapy. It will be understood, however, that the systems, devices, and methods described herein can be used in the context of other surgeries or even rehabilitation or physical therapy without surgical intervention. The sensors, described below, are placed near a physical therapy or rehabilitation site, such as a surgical site or the body portion to be rehabilitated.

The system may also provide alerts if patient tissue becomes inflamed or if the effectiveness of, or compliance to, physical or rehabilitation therapy is insufficient. The system includes a wearable device with one or more sensors. For example, one or more sensors may be provided on a wearable device that is applied to the skin of the patient.

In at least some embodiments, the one or more sensors communicate with a sensor processor on the device containing the sensors. In at least some embodiments, the sensor processor, or, alternatively or additionally, the sensors, communicate with a processor of a patient device, such as a mobile phone, tablet, computer or the like, or with a processor of a clinician device, such as a mobile phone, tablet, computer or the like.

Figure 1:
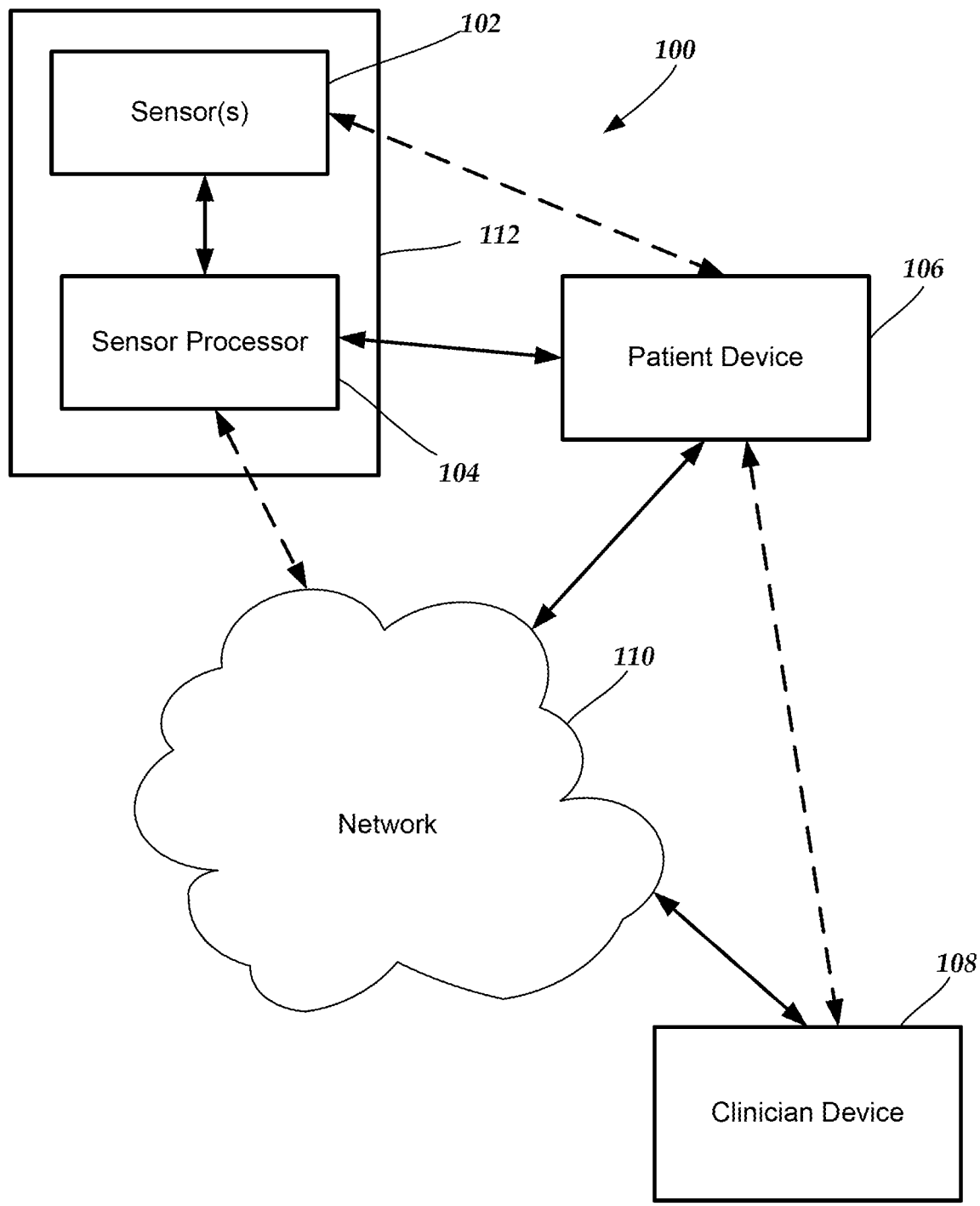
FIG. 1 is a schematic diagram of one embodiment of a system for monitoring rehabilitation of a patient after implant surgery, according to the invention.

FIG. 1 illustrates one embodiment of a system 100 for monitoring an orthopedic implant and rehabilitation after orthopedic replacement surgery. The system 100 includes one or more sensors 102, an optional sensor processor 104, a patient device 106 (such as a mobile phone, tablet, computer or the like), a clinician device 108, and a network 60. In at least some embodiments, the one or more sensors 102 and, preferably, the sensor processor 104 (or one or more of multiple sensor processors) are provided in a wearable device 112 that is external to the patient such as, for example, a device that is applied to the skin of the patient or is carried in a brace or other article or textile that is worn by the patient. Alternatively, one or more of the sensors 102 and, optionally, the sensor processor can be implanted in the patient. In some embodiments, one or more of the sensors 102 are implanted and a sensor processor and, optionally, one or more additional sensors are provided in a wearable device.

Other embodiments of the system may include fewer or more components than those illustrated in FIG. 1, but the system typically includes the sensor(s) 102 and a processor (such as sensor processor 104, patient device 106, or clinician device 108) to communicate with the sensor(s) and provide information based on the sensor data. In the illustrated embodiment, the wearable device 112 includes the sensors 102 and sensor processor 104, but it will be understood that other sensors may be included that are not part of the wearable device 112. For example, one or more additional sensors may be combined into another wearable device that may also include a sensor processor. It will also be understood that, in some embodiments, the wearable device 102 may not include a sensor processor 104 or the sensor processor 104 may have limited capabilities (such as, for example, obtaining and transmitting sensor readings without (or with limited) analysis of the sensor readings.

In FIG. 1, the solid lines indicate communication between components in at least some embodiments of the system. Dotted lines indicate alternative or additional modes of communication between components. In addition to the communication illustrated in FIG. 1, in at least some embodiments, the sensor processor 104 or sensors 102 may also communicate directly with the clinician device. Communications can include, but are not limited to, wireless communication, wired communication, optical communication, ultrasonic communication, or the combination thereof. Satellite communication, cellular communication, Bluetooth™, near field communications (NFC), Infrared Data Association standard (IrDA), wireless fidelity (WiFi), and worldwide interoperability for microwave access (WiMAX) are non-limiting examples of wireless communication that can be used for communications. Ethernet, digital subscriber line (DSL), fiber to the home (FTTH), and plain old telephone service (POTS) are non-limiting examples of wired communication that can be used for communications.

The network 60 can be any suitable type of network including, but not limited to, a personal area network (PAN), local area network (LAN), metropolitan area network (MAN), wide area network (WAN), the Internet, or any combination thereof. In at least some embodiments, the network 60 can be bypassed to provide direct connection between components. It will be understood that other devices, such as a server or server farm, memory storage device, or the like can be connected to the patient device 106 or clinician device 108 through the network 60 or directly. For example, a server may be coupled to the patient device 106 or clinician device 108 that stores patient or other medical information, applications, user interfaces, a web interface, or the like for access by the patient device 106 or clinician device 108.

The patient device 106 and the clinician device 108 can be any of a variety of devices, such as computers (for example, a notebook computer, a mobile medical station or computer, a server, a mainframe computer, or a desktop computer), mobile devices (for example, a cellular phone or smartphone, personal digital assistant, or a tablet), or any other suitable device. In at least some embodiments, the clinician device 108 can be incorporated into a medical station or system.

FIG. 2 illustrates one embodiment of a computing device 201 for use as the patient device 106 or clinician device 108. The computing device 201 includes a processor 214, a memory 216, a display 218, and an input device 220. The computing device 201 can be local to the user or can include components that are non-local to the computer including one or both of the processor 214 or memory 216 (or portions thereof). For example, in some embodiments, the user may operate a terminal that is connected to a non-local processor or memory.

The computing device 201 can utilize any suitable processor 214 including one or more hardware processors that may be local to the user or non-local to the user or other components of the computing device. The processor 214 is configured to execute instructions provided to the processor. Such instructions can include any of the steps of methods or processes described herein.

Any suitable memory 216 can be used for the computing device 214. The memory 216 illustrates a type of computer-readable media, namely computer-readable storage media. Computer-readable storage media may include, but is not limited to, nonvolatile, non-transitory, removable, and non-removable computer-readable media implemented in any method or technology for storage of information, such as computer readable instructions, data structures, program modules, or other data. Examples of computer-readable storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

Communication methods provide another type of computer readable media; namely communication media. Communication media typically embodies computer-readable instructions, data structures, program modules, or other data in a modulated data signal such as a carrier wave, data signal, or other transport mechanism and include any information delivery media. The terms "modulated data signal," and "carrier-wave signal" includes a signal that has one or more of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, Bluetooth™, near field communication, and other wireless media.

The display 218 can be any suitable display device, such as a monitor, screen, display, or the like, and can include a printer. The input device 220 can be, for example, a keyboard, mouse, touch screen, track ball, joystick, voice recognition system, camera, microphone, or any combination thereof, or the like.

Returning to FIG. 1, the sensor processor 104 can be any suitable processor including one or more hardware processors. The sensor processor 104 is configured to execute instructions provided to the processor. The sensor processor 104 is configured to receive sensor data from the sensor(s) and communicate with the patient device 106, network 60, clinician device 108, or any combination thereof. Optionally, the sensor processor 104 may also process or analyze the sensor data and may have instructions stored thereon to perform such processing or analysis including, for example, instructions to perform the steps of any of the processing or analysis described herein. In at least some embodiments, one or more of the sensor(s) 102 can each include a processor that perhaps some or all of the functions of the sensor processor 104.

The one or more sensors 102 are provided to monitor an orthopedic implant and surrounding tissue or monitor rehabilitation after orthopedic surgery whether an implant was required or not, or to provide preparatory therapy in advance of a surgery, or any combination thereof. This disclosure will use an orthopedic knee implant as an example, but it will be understood that other joint implants, such as, for example, implants for the shoulder, hip, ankle, wrist, or any other joint, or any other orthopedic device, such as an orthopedic spinal implant, whether joint replacement, joint resurfacing, soft tissue reconstruction, debridement, limb correction surgery, ligament replacement, or the like.

Any suitable type of sensor 102 can be used including, but not limited to, accelerometers, magnetometers, gyroscopes, proximity sensors, infrared sensors, ultrasound sensors, thermistors or other temperature sensors, cameras, piezoelectric or other pressure sensors, sonar sensors, external fluid sensor, skin discoloration sensor, pH sensor, microphone, or the like or any combination thereof. In at least some embodiments, the system 100 includes at least one, two, three, four, five, six, or more different types of sensors 102. The system may include at least one, two, three, four, five, six, eight, ten, or more sensors 102. Further examples of suitable sensors and their arrangement and use can be found at U.S. patent application Ser. Nos. 15/077,809 and 15/077,793 and U.S. Provisional Patent Application Ser. Nos. 62/136,892 and 62/136,925, all of which are incorporated herein by reference.

The one or more sensors 102 can be used to measure, monitor, or otherwise observe one or more aspects of the orthopedic device, surrounding tissue, or patient activity, or the like. The following are examples of observations or measurements that can be made or interpreted using one or more of the sensors: number of steps, repetitions of an exercise, repetitions of joint movement (e.g., joint pivoting), type of exercise being performed, or other actions; stability, or lack thereof; flexion angle or range of motion; rate of motion; temperature of skin; pulse or pulse profile or heart rate recovery time after activity; ultrasound images, flow measurements, or Doppler measurements; sonar images, flow measurements, or Doppler measurements; pressure or load bearing measurements; detection of a limp or body orientation (e.g., subluxation, posture, scoliosis) or a change in body orientation; joint shock or impact monitoring; sleep profile or rest duration; gait analysis, body/limb/joint alignments; or the like. A system 100 can observe or measure one or more of these items or any combination of the items.

The following provides further details on some of these measurements or observations. One or more sensors (for example, accelerometers, gyroscopes, magnetometers, proximity sensors, or the like) may count steps or repetitions of an exercise or number of joint movements or other actions experienced by the sensor, and may be utilized to determine what type of exercise or movement is occurring. This can be used, for example, to monitor patient activity, monitor compliance with exercise therapy, or monitor possible signs of pain or other conditions that may hinder or aid rehabilitation. The sensor data may also be used to monitor changes in activity or trends in activity.

One or more sensors (for example, accelerometers, gyroscopes, magnetometers, proximity sensors, or the like) may sense or detect or compute the range of motion of the sensor, joint, or other portion of the patient body or the flexion of the joint. This can be used, for example, to monitor patient rehabilitation, patient activity, monitor compliance with exercise therapy, or monitor possible signs of pain or other conditions that may hinder or aid rehabilitation. These sensors or other sensors may be used to monitor shock to, or impact on, the orthopedic device or tissue around the orthopedic device. The sensor data may also be used to monitor changes in range of motion or flexion or trends in range of motion or flexion.

As an illustrative example, one or more accelerometers can measure the acceleration from joint movement. A ratio of measured acceleration between accelerometers of known distance apart can be used to assess the joint movement and region of motion or flexion by calculating the center of rotation about which the device is being rotated. This information can be used for the same purposes as described in the preceding example.

In another illustrative example, 1) an accelerometer and 2) a gyroscope or magnetometer (which indicates direction relative to magnetic north) can be used to measure range of motion, rate of motion, number of repetitions, or the like. This information can be used for the same purposes as described in the preceding two examples.

In another illustrative example, a single sensor such as an accelerometer, gyroscope, or magnetometer can be used to measure or otherwise observe range of motion, rate of motion, number of repetitions, or the like. In at least some embodiments, these measurements or other observations are determined using the sensor data and one or more assumptions about the sensor or sensor data based on, for example, the recognition of patterns in the sensor data, the upper and lower limits of the range in the data collected, or the like.

Such information can be used in a manner similar to that in the preceding three examples.

One or more sensors (for example, thermistors or infrared sensors) may sense or detect or compute a temperature or a change in temperature or a temperature trend. The temperature may be a skin temperature or ambient temperature. The temperature measurements may be used, for example, to indicate the possibility of inflammation or pain or another condition that may hinder rehabilitation or patient health. The temperature measurement may also be used, for example, to monitor if icing is being performed effectively, which can help reduce inflammation and aid healing. These sensors may also or alternatively be used to sense, detect, or measure a pulse, a change in pulse, trends in the patient's pulse, a pulse profile, or heart rate recovery after patient activity (such as exercise or other exertion).

One or more sensors (for example, ultrasound or sonar sensors or cameras or the like) can sense or detect or compute particles or density of particles or a particle density trend. These sensors may also be used to sense the tissue surrounding the orthopedic device, detect wear or dimensional changes on the orthopedic device or surrounding tissue, or the like. Ultrasound and sonar sensors may also be used to determine how close other parts of the knee (or other joint) are to the implant.

One or more sensors (for example, piezoelectric, strain gage, or other pressure or load bearing sensors) can sense or detect or compute pressure or load with or around the sensor or orthopedic device. The sensor data may also be used to monitor changes in range of pressure or load bearing or trends in pressure or load bearing. These sensors or other sensors may be used to monitor shock to, or impact on, the orthopedic device or tissue around the orthopedic device. A pressure or load bearing sensor may also be used to detect swelling of the tissue around the orthopedic implant. Multiple pressure or load bearing sensors may also be used to detect flexion (which may be indicated by a uniaxial stretching of the tissue) and swelling (which may be indicated by biaxial stretching of the tissue.)

U.S. patent application Ser. Nos. 15/077,809 and 15/077,793 and U.S. Provisional Patent Application Ser. Nos. 62/136,892 and 62/136,925, all of which are incorporated herein by reference, describe examples of sensors (including arrangements with implantable sensors), systems, devices, and methods for monitoring rehabilitation. Further examples of sensors and their use can be found in U.S. patent application Ser. No. 15/422,312 and U.S. patent application Ser. No. 15/422,299, both of which are filed on even date herewith and incorporated herein by reference.

Power can be provided to the sensors 102 and optional sensor processor 104 using any suitable power source including, but not limited to, primary cells, rechargeable batteries, storage capacitors, other power storage devices, or the like or any combination thereof. In some embodiments, the power can be provided by a kinetic energy power source that utilizes the movements of the patient's body to generate power for the components or to or to charge a battery or storage capacitor or other power storage device coupled to the components. In some embodiments, wireless power sources can be used in place of (or in addition to) the battery, storage capacitor, or other power storage device.

In addition, a charging port can be provided for charging the battery or storage capacitor or other power storage device from a source such as a wall socket. Alternatively or additionally, wireless charging systems and methods can also be used. It will be understood that in some embodiments there may be multiple methods for providing power to the component or to a power storage device associated with the component. All of the sensors and optional sensor processor may be coupled to the same power source or some of the sensors (or even all of the sensors) and sensor processor may have individual power sources.

In at least some embodiments, the sensors and optional sensor processor can be active at all times to measure, monitor, or otherwise observe. In other embodiments, one or more of the sensors and optional sensor processor can be active periodically (with a period of, for example, 15 or 30 seconds or 1, 5, 10, 15, or 30 minutes or 1, 2, 3, 4, 6, 7, or 24 hours) or randomly to measure, monitor, or otherwise observe. Optionally, the period may be programmable. In addition, the period may be optionally altered based on data from one or more of the sensors. In yet other embodiments, one or more of the sensors and optional sensor processor may be activated manually or automatically by the sensor module, patient device, clinician device, or other device. In at least some embodiments, the sensors and optional sensor processor may have different activation schedules (continuous, periodic, random, or manual). For example, a sensor to measure temperature may do so periodically, a sensor to measure number of steps or movement of the joint may be continuous, and a sensor to measure range of motion may be activated manually by the wearable device, patient device, or clinician device when the patient performs rehabilitation exercises.

The systems and methods will be described herein with reference to an orthopedic knee implant or other knee surgery. Similar systems and methods can be used with other joints including, but not limited to, the finger joint, wrist joint, elbow joint, shoulder joint, hip joint, ankle joint, or toe joint. The systems and methods can be used to monitor physical therapy for any reason including, but not limited to, rehabilitation associated with other treatments including treatments for ligament or fracture surgery.

FIGS. 3A-3C illustrate one embodiment of a wearable device 312 that includes a sensor unit 322 and a base 324. The sensor unit 322 is removable from the base 324, as illustrated in FIG. 3A. The wearable device 312, as illustrated in FIGS. 3B and 3C, is disposed on the patient's skin with the base 324 adhered to the skin.

The base 324 includes a flexible receiving shell 326, a magnet 328, an optional opening 330 for a temperature sensor, an optional tab 332, adhesive disposed on a bottom surface 334 of the shell, and an optional magnet holder 336 disposed on the shell. The magnet 328 of the base 324 magnetically attaches to a similar magnet 354 (FIG. 4C) in the sensor unit 322 when the sensor unit 322 is attached to the base 324. The magnets 328, 354 are intended to maintain attachment of the sensor unit 322 to the base 324 during normal activity, exercise, and other physical therapy unless a patient or other person disengages the sensor unit from the base. Optionally, a magnet holder 336 fits over (entirely or only a perimeter of) the magnet 328 to hold the magnet to the shell 326.

In at least some embodiments, the shell 326 of the base 324 is sufficiently flexible for adhesion to the skin of a patient as the patient moves during normal activity or physical therapy exercises. The shell may be made of any suitable material including, but not limited to, flexible plastics such as silicone or polyurethane.

The shell 326 may also removably grip the sensor unit 322 to provide further maintenance of the attachment of the sensor unit to the base 324. In the illustrated embodiment, the shell 326 defines a receiving cavity 338 with sidewalls 340 around the cavity and a rim 342 around the sidewalls.

In operation, the shell 326 receives a portion of the sensor unit 322, as illustrated in FIGS. 3B and 3C. In some embodiments, the sidewalls 340 or rim 342 may be resiliently flexible to expand when the portion of the sensor unit 322 is received in the cavity 338 and then compress against a perimeter of the received portion of the sensor unit 322. Preferably, at least the rim 342 or sidewalls 340 (or both) of the base 324 are made of a material that grips the sensor unit 322 by adhesion, compression, or the like or any combination thereof. In at least some embodiments, the sensor unit 322 may have a groove 390 that can receive the rim 342 to further facilitate maintaining the attachment of the sensor unit to the base 324. In at least some embodiments, the sidewalls 340 slope outwardly and downwardly from the rim 342 to form an undercut region below the rim. The sensor unit 322 can be similarly formed with a sloping housing to fit in the undercut below the rim 342 of the base 324 to further facilitate maintaining engagement between the sensor unit and the base. It will be recognized that in addition or as an alternative to the magnets (or magnet and magnetically attracted material) any other suitable type of mechanical fastener can be used to fasten the sensor unit 322 to the base 324.

The adhesive can be applied to the base 324 or can be an adhesive disposed on two sides of a substrate with one side of the substrate adhered to the base 324. Preferably, the adhesive is selected to be water resistant and resist losing adherence due to contact with sweat. In at least some embodiments, the base 324 or the adhesive on the base is intended for use for at least one, two, three, five, seven, or ten days or two, three, or four weeks or more under normal usage conditions before replacement or reapplication of adhesive. In at least some embodiments, the adhesive is selected to maintain adhesion to the skin when the user takes a shower. In at least some embodiments, the adhesive is selected to maintain adhesion to the skin when the user takes a bath, swims in a pool, or sits in jacuzzi, hot tub, or rehabilitation pool.

The base 324 optionally includes a tab 332 disposed at any suitable position relative to the shell 326. The tab 332 can facilitate removal of the sensor unit 322 from the base 324 by pushing or pulling on the tab 332 to deform the shell 326 to free the sensor unit. Preferably, operation of the tab 332 to disengage the sensor unit 322 can be performed while maintaining attachment of the base 324 to the skin of the patient. In some embodiments, operation of the tab 332 can also facilitate engagement of the sensor unit 322 with the base 324.

Figure 4C:
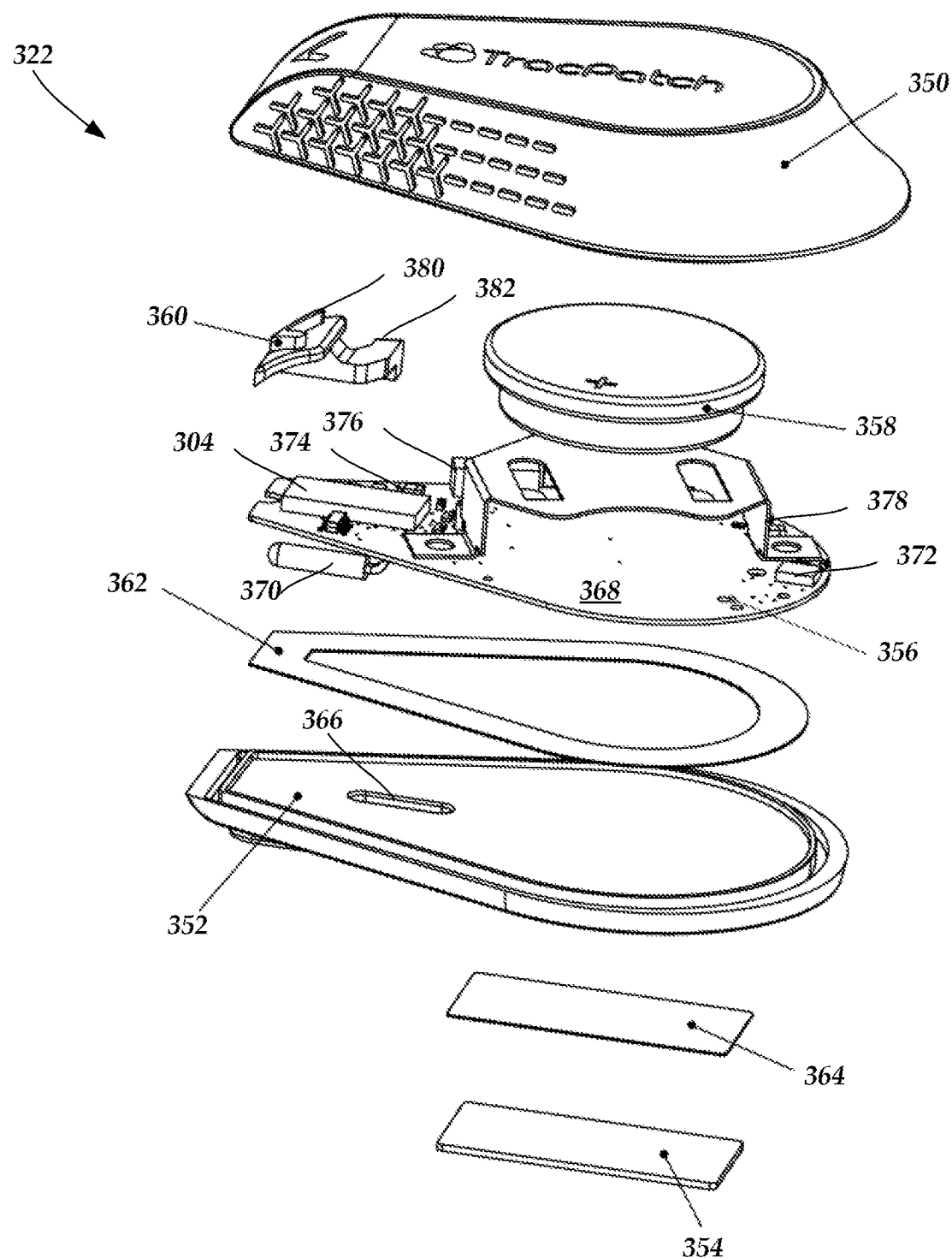
FIG. 4C is an exploded view of the sensor unit of FIG. 4A, according to the invention.
Figure 4D:
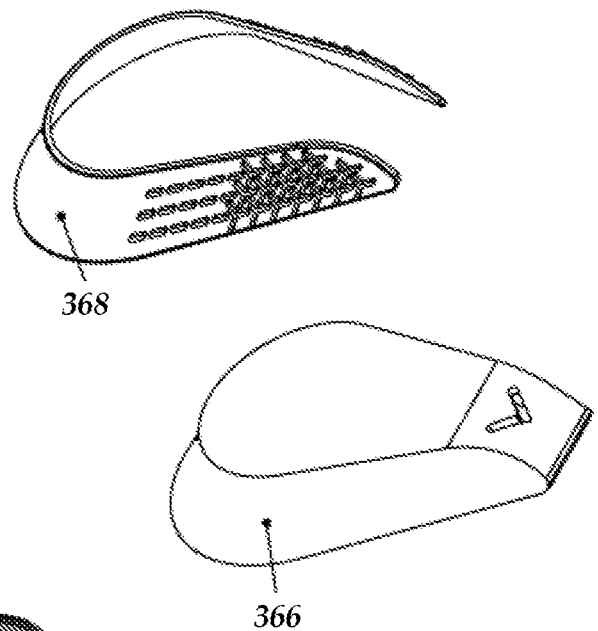
FIG. 4D is an exploded view of one embodiment of a housing of the sensor unit of FIG. 4A, according to the invention.

FIGS. 4A-4C illustrate one embodiment of a sensor unit 322. The illustrated sensor unit 322 includes an upper housing 350, a lower housing 352, a magnet 354, an electronics assembly 356, a power source 358, a light emission arrangement 360, and adhesive 362, 364. In addition, in some embodiments, as illustrated in FIG. 4D, the upper housing 350 can include a main housing 366 and a gripping element 368. In some embodiments, the sensor unit 322 can include more or fewer components than those illustrated in FIGS. 4A-4D.

The upper housing 350 and lower housing 352 form a cavity within which at least the electronics assembly 356 and power 358 source reside. The upper housing 350 and lower housing 352 can be made of any suitable material, such as metal or plastic materials (preferably, rigid plastic materials) or any combination thereof. In at least some embodiments, the upper housing 350 and lower housing 352, as well as the joining of the upper housing to the lower housing, are water resistant to resist ingress of water, sweat, rain, and other fluids into the interior of the housing. In at least some embodiments, the sensor unit 322 is sufficiently water resistant to allow the patient to shower without any covering over the sensor unit. In some embodiments, the sensor unit 322 is sufficiently water resistant to allow the patient to bathe or swim without any covering over the sensor unit.

The optional gripping element 368 can have a roughened or otherwise non-smooth surface on at least a portion of the gripping element. This non-smooth surface facilitates gripping of the sensor unit 322, particularly for engaging or disengaging the sensor unit from the base 324. In the illustrated embodiment, the gripping element 368 is a separate element that is overmolded, adhered, or otherwise attached to the main housing 366. The gripping element 368 may be made of a different, more flexible material than the main housing 366, such as silicone or polyurethane. In other embodiments, the gripping element 368 is formed as part of the main housing 366 by roughening or otherwise making at least a portion of the surface of the main housing non-smooth.

The magnet 354 is arranged for magnetically coupling to the magnet 328 of the base 324. In some embodiments, one of the magnets 354, 328 can be replaced with a magnetically attracted material that will then couple with the other magnet 354, 328 to magnetically coupled the base 324 to the sensor unit 322. In the illustrated embodiment, the magnet 354 is attached to the lower housing 352 by adhesive 364 which can be a layer of adhesive or adhesive disposed on both sides of a substrate. In other embodiments, the magnet 354 may be attached to the lower housing 352 by any other suitable method or may be disposed within the cavity formed by the upper housing 350 and lower housing 352.

The power source 358 can be any suitable power source. For example, the power source 358 can be a primary cell (e.g., a battery) and may have an expected lifetime, under normal usage, of at least 7, 10, 20, 30, 60, 90, 100, 70, or 180 days or more. In some embodiments, the primary cell may be replaceable. In some embodiments, the power source 358 is rechargeable using, for example, a recharge port or an inductive recharge device (such as an inductive mat or sleeve), or using WiFi or ultrasonic charging or any other suitable recharging method. In some embodiments, the primary cell (e.g., battery) can be the magnetically attractive material that the magnet 328 of the base 324 can be magnetically coupled to.

The electronics assembly 356 can contain any suitable components for operation of the sensor unit 322. In the illustrated embodiment, the electronics assembly 356 comprises a circuit board 368, a sensor processor 304, a temperature sensor 370, an accelerometer 372, at least one LED 374, a communications arrangement 376, and a magnetic switch 378. Adhesive 362 can couple the circuit board 368 to the lower housing 352. Other adhesive (not shown) may couple the circuit board or other components to the upper housing 350.

The sensor processor 304 can be similar to the sensor processor 104 described above and may have more or fewer capabilities than that sensor processor 104. In some embodiments, the sensor processor 304 may include analysis algorithms for analyzing or partially analyzing the sensor data. In other embodiments, the sensor processor 304 may be primarily designed to receive, store, and transmit sensor data.

The illustrated sensor unit 322 includes a temperature sensor 370 and an accelerometer 372, but other embodiments can contain more or different sensors, in any suitable combination, as described above. In the illustrated embodiment, the temperature sensor 370 is a thermistor which extends away from the circuit board 368 and through an opening 366 in the lower housing 352. When the sensor unit 322 engages the base 324, a portion of the temperature sensor 370 extends through the opening 330 in the base 324 so that the temperature sensor 370 is exposed to the skin of the patient and may be in contact with the skin of the patient.

The communications arrangement 376 operates with the sensor processor 304 to communicate with patient or clinician devices or other devices, as described above. Any suitable communications method or protocol can be used including, but not limited to WiFi, Bluetooth™, near field communications, infrared, radio frequency, acoustic, optical, or the like.

In some embodiments, the electronic assembly 356 also includes a magnetic switch 378, such as a reed switch, that is coupled to the sensor processor 304 so that when positioned near the magnet 328 of the base 324 is actuated to place the sensor unit 322 in an active mode. In at least some embodiments, when the sensor unit 322 is removed from the base 324 the magnetic switch is actuated to place the sensor in an inactive or standby mode. Alternatively or additionally, the sensor unit 322 may include a button, mechanical switch, or other mechanism to place the sensor into the active mode or into an inactive or standby mode or to toggle between modes or to turn the sensor unit on or off. Also, alternatively or additionally, the sensor unit 322 may be placed into the one of these modes (or toggled between modes) using signals from a patient or clinician device or other device communicating with the sensor unit 322. In at least some embodiments, in the inactive or standby mode, the sensor unit 322 continues to be receptive to signals from an external source (such as the patient or clinician device). In at least some embodiments, in the inactive or standby mode, the sensor unit 322 also maintains an internal clock.

The at least one LED 374 is coupled to the light emission arrangement 360 to provide light to the light emission arrangement. In at least some embodiments, the light emission arrangement 360 includes a light emitter 380 and a light pipe 382 to direct light from the LED(s) 374 to the light emitter. The light emission arrangement 360 provides an indication of operation of the device to a user or patient. For example, the light emission arrangement 360 may be lit when the sensor unit 322 is operating or is in the active mode. In some embodiments, the color of light emitted by the light emission arrangement may indicate which mode (active or inactive/standby) the sensor unit is currently in or may indicate operations being performed by the sensor unit (for example, transmitting, sensing, not sensing, synching with a patient or clinician device, or the like). In some embodiments, instead of, or in addition to, color, flashing of the light or brightness of the light may be used to indicate mode or operations. As an example, a flashing blue light may indicate synching with a patient or clinician device, a green light may indicate the active mode, and the absence of light may indicate the inactive/standby mode.

U.S. patent application Ser. Nos. 15/077,809 and 15/077,793 and U.S. Provisional Patent Application Ser. Nos. 62/136,892 and 62/136,925, all of which are incorporated herein by reference, describe additional features and arrangements that can be incorporated in the wearable devices and sensor units described herein. These patent applications also describe other wearable or implantable devices that can be used in the methods and systems described herein.

In some embodiments, a second sensor unit can be used. For example, the second sensor unit can be placed on or within the same leg on the other side of the joint. As another example, a second sensor unit may be placed on the other leg for use in detecting or observing limp or other gait deficiencies or placed on the torso to detect or observe body orientation. A second sensor unit (or more additional sensor units) may also be used when two or more replacements are implanted in the body, for example, with multiple joint or vertebra replacements, to detect or observe, for example, subluxations, changes or defects in posture, scoliosis, or the like.

The two sensor units optionally can communicate or synch with each other. In at least some embodiments, the two sensor units can sync to each other and know where each one is in space and their location from each other in terms of distance and orientation. As an example, the two sensor units may triangulate their positions using a patient or clinician device. In at least some embodiments, if one of the sensor units is replaced or removed from its base, the patient device or other sensor unit is advised. When the sensor unit is reattached to its base or a new sensor unit is attached to the base, the system can determine the location or distance of the new sensor unit relative to the other sensor unit.

The sensors in the two sensor units can be used to measure flexion angles; range of motion; calculate vectors, angles, rays, planes or distances; and the like. Temperature sensors on the two sensor units can be used to determine temperature differences between two portions of the body. The sensors from the two sensor units can be used to calculate angles or other information that can be used to send signals to the patient if the patient is exceeding limitations on movement of range of movement during physical therapy or rehabilitation.

As indicated above, the sensor processor or sensor communicates with a patient device or clinician device to provide sensor data or information derived from the sensor data. The patient device can be a dedicated device or can be an application on a smartphone, tablet, laptop or desktop computer, a web or cloud application, or any other suitable arrangement. Communication between an implanted or wearable sensor unit and the patient or clinician device can occur at predetermined times (for example, every 30 minutes or every hour or once a day). In this manner, the sensor unit can sync with the patient or clinician device. Similarly, the patient device may sync with the clinician device on a regular schedule. In some embodiments, if the sensor unit or patient device detects a situation (such as a fall or elevated temperature) where an alert is warranted, the sensor unit or patient device may communicate (or attempt to communicate) with the patient device or clinician device, respectively, immediately to provide a warning.

Alternatively or additionally, the communication between the sensor unit and the patient or clinician device can be constant or nearly constant (for example, once every 1, 5, 10, 30, or 60 seconds.) For example, the constant or near constant communication may be established when the sensor unit determines that the patient is performing exercises or when the patient manually actuates a control on the patient device or sensor unit indicating that the patient will commence with exercises or otherwise desires the sensor unit to communicate or sync with the patient device.

FIGS. 5-16 illustrate screenshots of one embodiment of an application or user interface for the patient device or clinician device. The illustrated application or user interface is particularly useful for a mobile device such as a smartphone or tablet, but can also be used with other devices such as desktop or laptop computers. FIG. 5 illustrates one embodiment of a patient or clinician profile for the application or user interface. Elements of this page can include, but are not limited to, patient or clinician information, controls to input an identification number or other identification information for a wearable device so that the wearable device can be synched or otherwise coupled to the patient or clinician device, controls to input or change a password or to input or access application settings, a control to access a calibration program to calibrate the wearable device, controls for accessing one or more other features or pages, or the like. Other information that might be presented on this or another page can include, but is not limited to, controls for account creation or account login, indication of the status of the wearable device, or controls to access help information; FAQs; photos or videos or text for directions on how to apply the wearable device to the skin of the patient, how to care for a surgical wound, how to perform particular exercises, or how to program or operate the wearable device.

Figure 6:
FIG. 6 is a diagram of one embodiment of a user interface for a mobile device to display information obtained from a sensor unit, according to the invention.

FIG. 6 illustrates another page of the user interface or application that provides information such as steps per day (or number of repetitions of an exercise or the like) and a temperature measurement as shown in section 592. The user interface 590 may also include a section 594 that shows graphs of the data such as the hourly number of steps, as illustrated in FIG. 6. The illustrated user interface permits the user to select from other charts such as exercise history (labeled "ROM"), temperature or temperature trends, and number of impacts or shocks to the sensor module. It will be understood that other measurement or observations from the sensor described above can be graphed. In at least some embodiments, the user may also be able to select the time period of the graph to display data in periods of time such as, for example, minutes, hours, days, or weeks.

This user interface can be useful in monitoring patient activity and progress. The graphs in section 594 may be useful for showing patient exercise history and progress. In some embodiments, the user interface may also allow the user to set goals such as, for example, a number of steps or a number of exercise repetitions over a particular period (for example, 1, 2, 4, 6, or 7 hours or 1 day or 1 week). The user interface may also display the current status towards attaining those goals. The user interface may also highlight notable events, such as, for example, the largest number of steps or exercise repetitions, elevated temperature readings, large numbers of impacts or shocks, or the like. The user interface may also highlight the attainment of goals.

Figure 7:
FIG. 7 is a diagram of another embodiment of a user interface for a mobile device to display information obtained from a sensor unit, according to the invention.

FIG. 7 illustrates another page of the user interface or application that displays information related to particular patient measurements that can be tracked to monitor rehabilitation or physical therapy. In the illustrated page, the patient measurements are flexion and extension related to a patient's knee. These patient measurements can include, but are not limited to, range of motion measurements such as flexion and extension. The page also illustrates a chart 596 tracking the progress of these measurements. The progress may be tracked hourly, daily, weekly, or over any other period of time. In some embodiments, the user interface or application allows the user to select or change the time period illustrated in the chart. The page in FIG. 7 also provides information about other measurements such as percentage of exercise completion, skin temperature, number of steps or the like.

Figures 8, 9:
FIG. 8 is a diagram of one embodiment of a user interface for a mobile device to display a range of motion measurement, according to the invention.
FIG. 9 is a diagram of one embodiment of a user interface for a mobile device to display a summary of repetitions of exercises, according to the invention.

FIG. 8 illustrates another page in which the user interface or application can be directed to calculate or otherwise determine a particular measurement. In the illustrated case, the measurement is femur angle.

FIG. 9 illustrates another page in which the user interface or application tracks the daily exercise program. In the illustrated embodiment, the exercises are sitting lift, heel slide (hip and knee flexion), straight leg raise, and knee to chest. Other exercises can include, but are not limited to, standing lift, ankle pump, ankle circle, thigh squeeze (quadriceps set), lying kick (short arc quadriceps), knee bend (sitting knee flexion), prolonged knee stretch, sitting kick (long arc quadriceps), keen straightening stretch, knee dangling/swinging, hamstring set (heel dig), buttocks squeeze (gluteal set), walking, or the like. These exercises are directed to knee rehabilitation. Of course, rehabilitation or physical therapy for other joints or body regions can include a different set of exercises. In addition, the page illustrates the percentage of completion for each set of repetitions (in this case, three sets) that are to be performed by the patient.

Figures 10, 11:
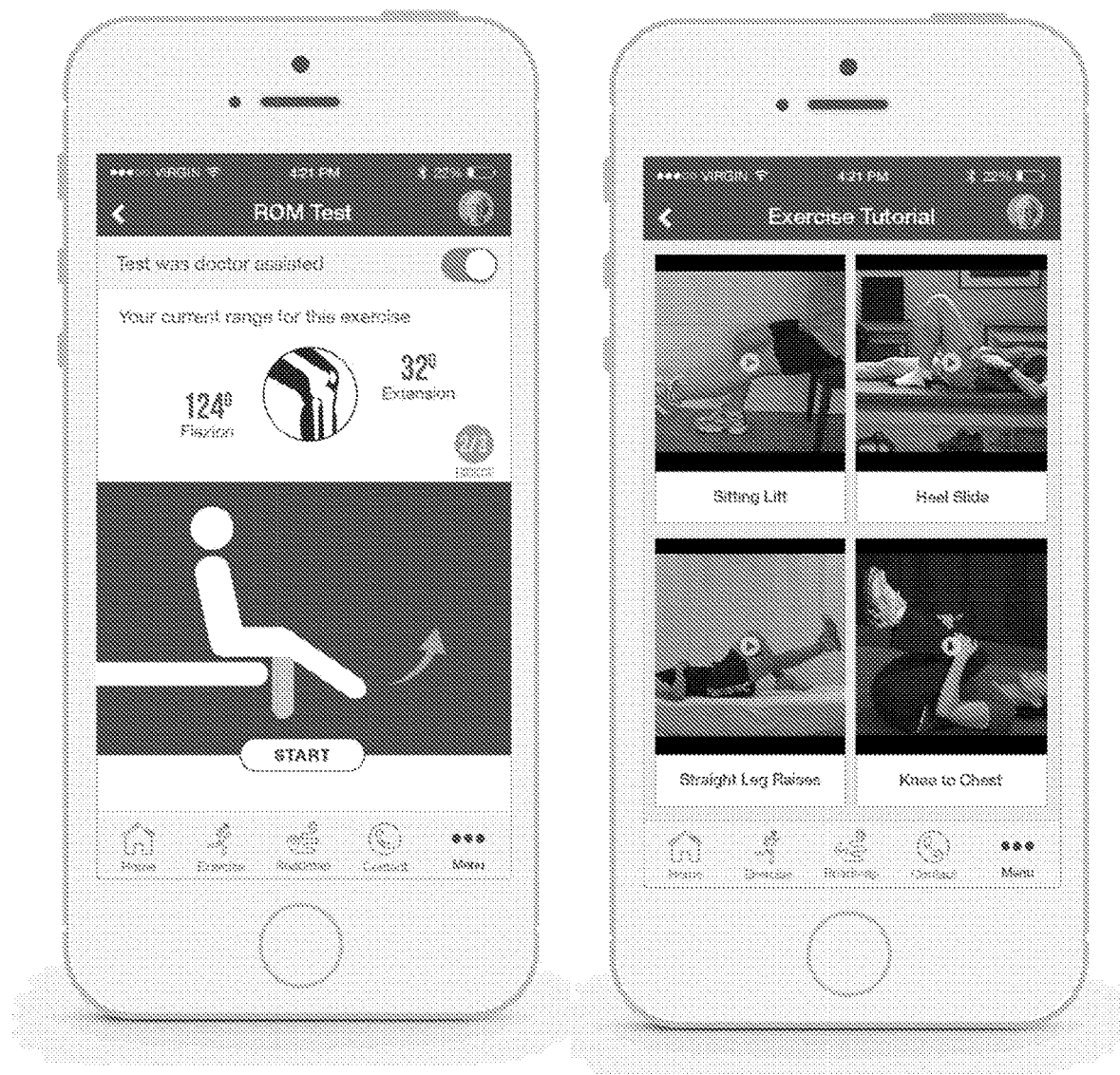
FIG. 10 is a diagram of one embodiment of a user interface for a mobile device to display information obtained from a sensor unit, according to the invention.
FIG. 11 is a diagram of one embodiment of a user interface for a mobile device to display selectable videos to demonstrate exercise, according to the invention.

FIG. 10 illustrates yet another page with a single exercise. This page illustrates the current measurements associated with the exercise (in this case, flexion and extension). The page also illustrates how the exercise is performed and may include a control for the patient to indicate that the exercise is to be begun. In some embodiments, the page may also provide an indication of the number of repetitions (or the number of repetitions that are still needed to achieve a repetition goal) as the patient exercises. The page may also indicate patient measurements based on the exercise (e.g., a current measurement for the latest repetition or an average measurement for the current set of repetitions or a maximum measurement for a set of repetitions) and may also indicate a goal for the measurement. This page may include a meter with bars or the like to indicate what portion of an exercise goal has been met. An indication (such as a bar or the like) may also indicate what portion of a range of motion or other therapy goal has been met. In some embodiments, the page may display an average patient time to the range of motion goal or the like to motivate the patient.

Figure 12:
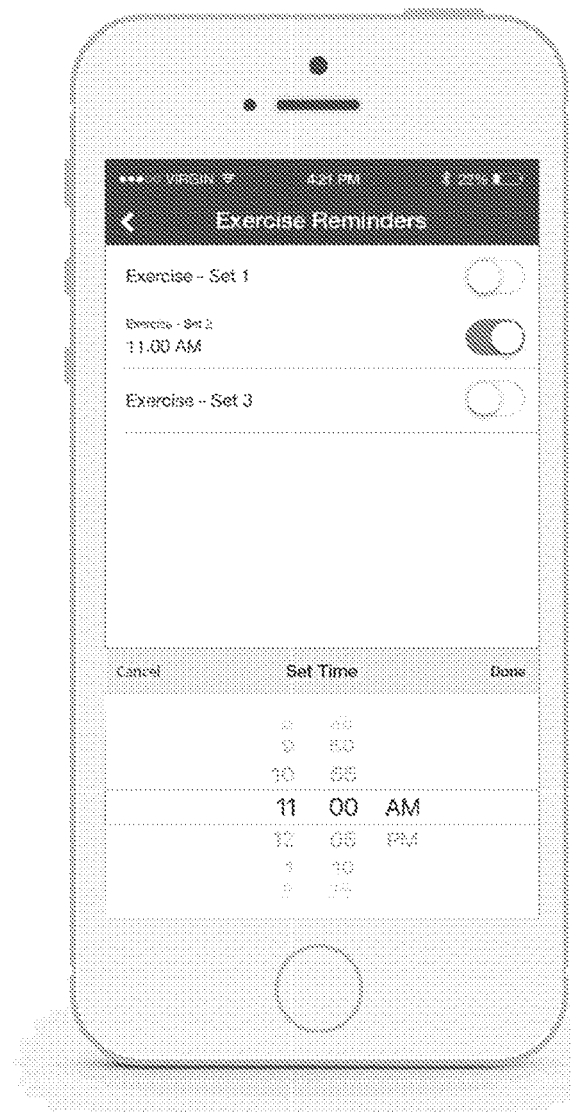
FIG. 12 is a diagram of one embodiment of a user interface for a mobile device to set an exercise reminder, according to the invention.

FIG. 11 illustrates a page with controls for accessing videos that can show the patient how to perform exercises. FIG. 12 illustrates a page where the patient can set reminders to perform an exercise. The patient can set a time for the reminder and may also set a visual or audible alarm to remind the patient to exercise at the appointed time.

Figure 13:
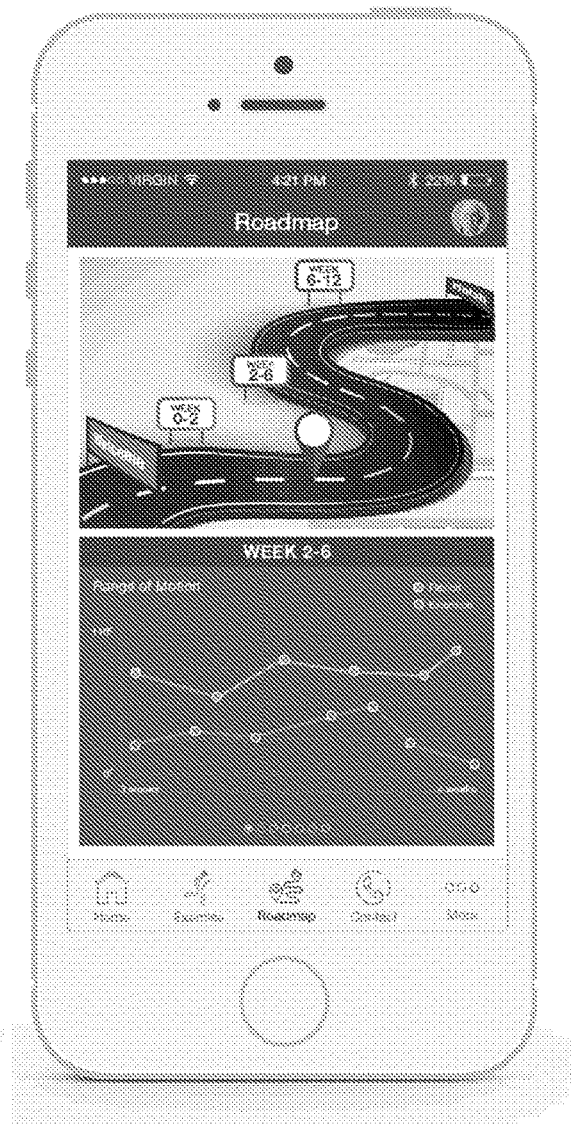
FIG. 13 is a diagram of one embodiment of a user interface for a mobile device to display information obtained from a sensor unit and a pathway toward a physical therapy goal, according to the invention.

FIG. 13 illustrates a page with an indication of how far the patient has progressed in the physical therapy or rehabilitation. The distance and milestones included on this indication can be based on time (e.g., days or weeks) of the rehabilitation; physical measurements (e.g., flexion or extension) towards a final goal for that physical measurement; number of completed repetitions, or completion of, one or more exercises towards an exercise goal, or the like. As illustrated in FIG. 13, the page may also include a graph of measurements (similar to FIG. 7) or number of repetitions or a graph of any other pertinent information.

Figure 14:
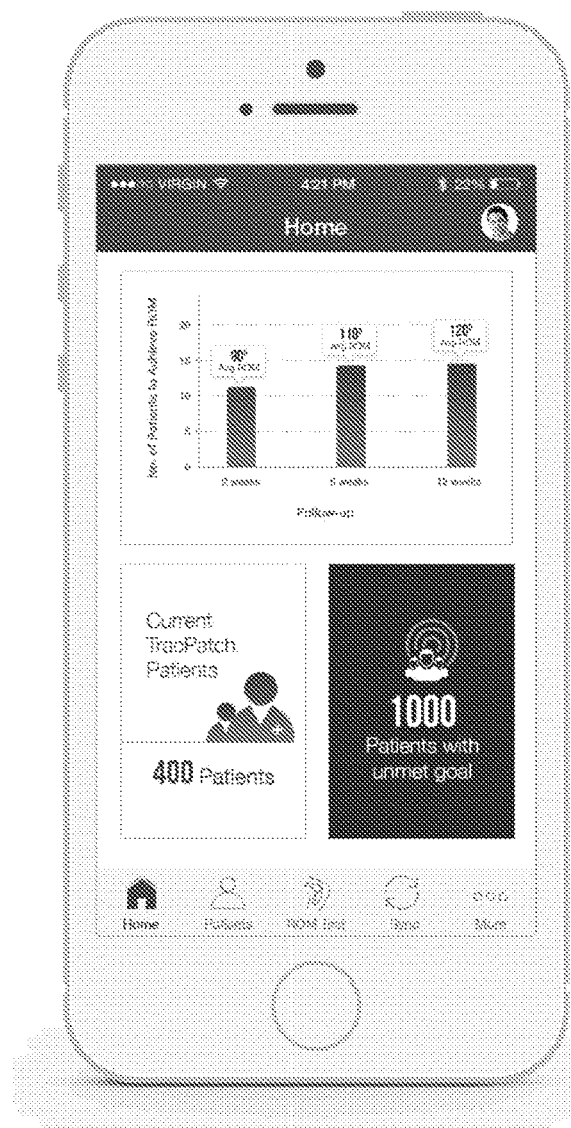
FIG. 14 is a diagram of yet another embodiment of a user interface for a mobile device to display information obtained from a sensor unit, according to the invention.

FIG. 14 illustrates a page for a clinician device that indicates information about a group of patients, such as number or percentage of patients completing exercise or other goals, number or percentage of patients achieving particular range of motion or other measurement goals, or the like.

Figure 15:
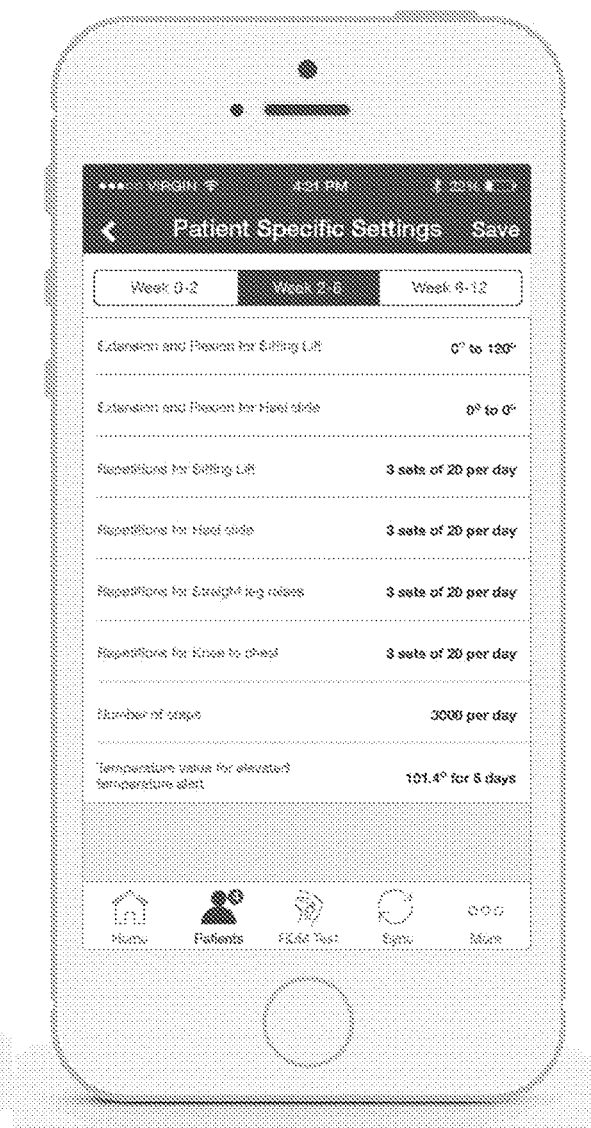
FIG. 15 is a diagram of one embodiment of a user interface for a mobile device to set patient specific settings for a sensor unit, according to the invention.

FIG. 15 illustrates a page for a patient or clinician device where settings can be entered or changed for a patient. Such settings can include, for example, which exercises are to be performed, number of repetitions for each exercise, number of sets of repetitions per day for each exercise, number of steps for each day. This page may include controls to permit changing these settings. In addition, as illustrated in FIG. 15, the settings may be related to a particular stage of the rehabilitation or physical therapy. The page may allow for toggling between different stages sot that settings can be viewed, entered, or changed for that stage. Another page for a patient or clinician device may display the actual results achieved by the patient and may compare those to the settings or goals entered for that patient.

Figure 22:
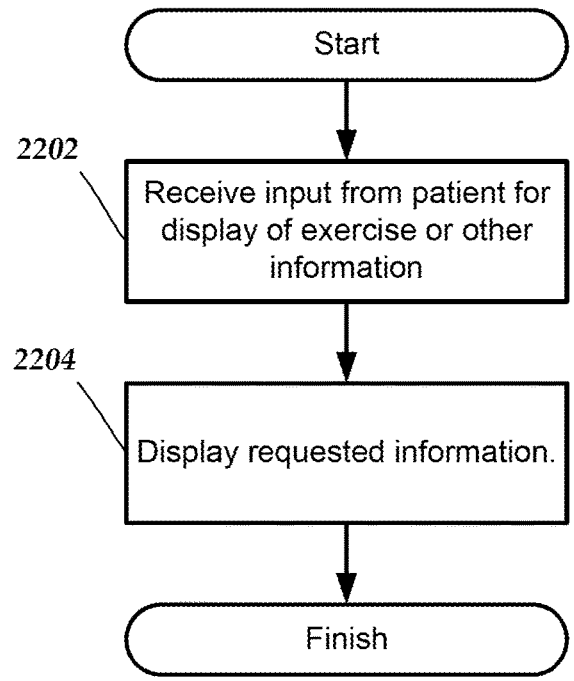
FIG. 22 is a flowchart of one embodiment of a method for displaying information requested by the patient; according to the invention.

FIG. 22 illustrates one embodiment of a method for displaying information requested by the patient. In step 2202, the patient device receives input from the patient for display of exercise or other information. In step 2204, the patient device displays the requested information. For example, the requested information may be a graphical representation of the exercise and a user control which, when actuated by the user, indicates that the user is performing the exercise. One example of such requested information is illustrated in FIG. 10. The requested information may be a count of repetitions of the exercise being performed or a summary of a plurality of exercises indicating a number of repetitions performed for each exercise over a period of time. Examples of such requested information are presented in FIGS. 7, 9, 13, and 14. The requested information may be a progress report for a range of motion measurement or a graph of values for the range of motion measurement obtained over a period of time. Examples of such requested information are presented in FIGS. 7, 13, and 14. The requested information may be a representation of a pathway to a goal for the range of motion measurement with an indication of current progress of the patient toward that goal as illustrated, for example, in FIG. 13.

Figure 16:
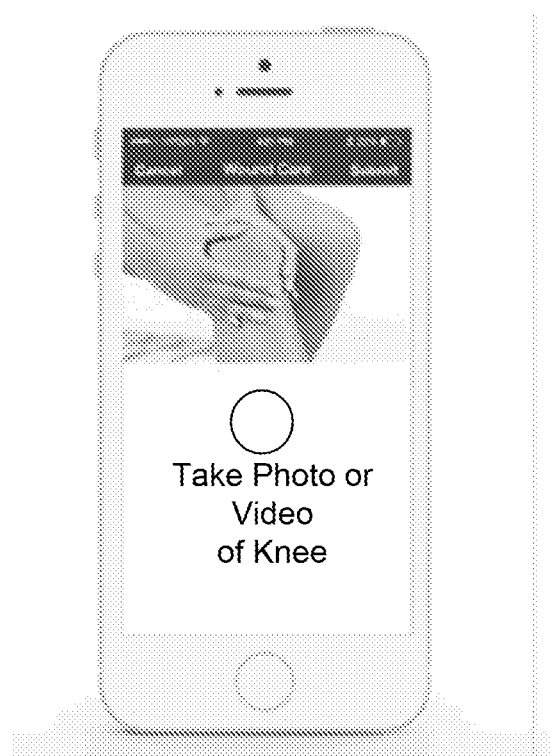
FIG. 16 is a diagram of one embodiment of a user interface for taking a photograph or video, according to the invention.

FIG. 16 illustrates another page in which the patient is directed to take a photograph or video of their knee or other wound site or physical therapy site using a camera on the patient device or other device. The page may direct the user how to frame the photo or video. In at least some embodiments, the photo or video may be sent to the clinician device or other device through the network (see, FIG. 1) or by other methods. A clinician may use the photo or video to assess the wound or physical therapy site. In some embodiments, the patient device may request a video be taken of the patient performing an exercise. The video may be provided to the patient device or clinician device to assess or view performance of the exercise. For example, a clinician may assess whether the patient is performing the exercise correctly or may assess progress in physical therapy or rehabilitation by observation of the exercise.

In some embodiments, the patient device is configured and arranged to perform pigment analysis or other wound analysis on the knee using the photo or video. For example, the patient device may compare skin pigment at the wound site with skin pigment near the wound site to identify infection (for example, superficial wound infection or deep wound infection), rash, discoloration, or other issues. In at least some embodiments, the pigment or other wound analysis may be combined with skin temperature information to assess infection (for example, superficial wound infection or deep wound infection), rash, discoloration, or other issues. If the analysis indicates a potential or actual issue, the patient device may provide a visual or audible warning to the patient and may also send an alert to the clinician device. In other embodiments, the pigment or other wound analysis (with or without skin temperature information) may be performed by the clinician device or other device instead of (or in addition to) the patient device. The patient device or clinician device may include white balancing or light compensating algorithms to assess the photos or videos. The patient device may also include a calibration tool to facilitate calibrating the light and other aspects of the photo or video.

In some embodiments, instead of or in addition to taking a photo or video, the patient device may display the region at which the camera is pointed for viewing by the patient. This displayed area, or the photo or video, may be altered to overlay lines or graphics that correspond to patient anatomy. These lines or graphics may move as the patient's leg or other body part move. In some embodiments, patient measurements, such as flexion or extension or other range of motion measurements, may be calculated during the movement and displayed on the patient device; changing as the patient limb moves.

Figure 20:
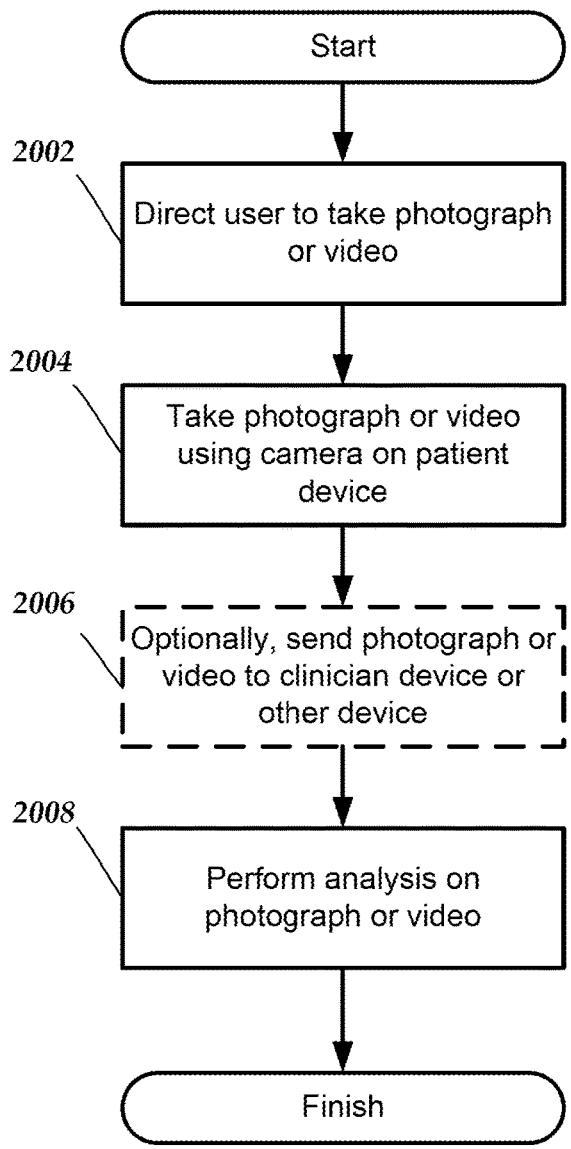
FIG. 20 is a flowchart of one embodiment of a method of taking a photograph or video of a site on the patient; according to the invention.

FIG. 20 describes one embodiment of a method of taking a photograph or video of a site on the patient. In step 2002, the patient device (or clinician or other device or person) directs the patient to take photograph or video of the site (such as the site of physical therapy or a surgical or wound site.) In step 2004, the patient takes the photograph or video using the camera of the patient device (or a camera of another device) and the photograph or video is stored. In some embodiments, the photograph or video is sent to the clinician device or other device, in optional step 2006. In step 2008, analysis can be performed on the photograph or video. The analysis can be performed by the patient device, clinician device or any other suitable device. For example, a pigment analysis can be performed or analysis related to exercises or range of motion measurements can be performed. In some embodiments, graphical indicia, such as lines or angles, can be superimposed on the photograph or video based on the analysis.

A patient device, user interface, or application may include other features. For example, the patient device, user interface, or application may include controls for a patient to enter information or ratings about their experience in the hospital, their experience during rehabilitation, how connected the patient fees during the rehabilitation process, whether the patient would recommend the wearable device or other aspects of the treatment to family or friends, or the like. The patient device, user interface, or application may include controls for entering a rating related to pain or other clinical aspects. For example, the patient may enter a pain score based on a scale provided on the device. Other scores that may be entered by the patient, clinician, or others may be based on scores such as a Knee Society score, a New Knee Society score, other society score, KOSS or PROM (patient reported outcome measurements), oxford knee score, or Womack, or any other suitable score or rating.

Figure 21:
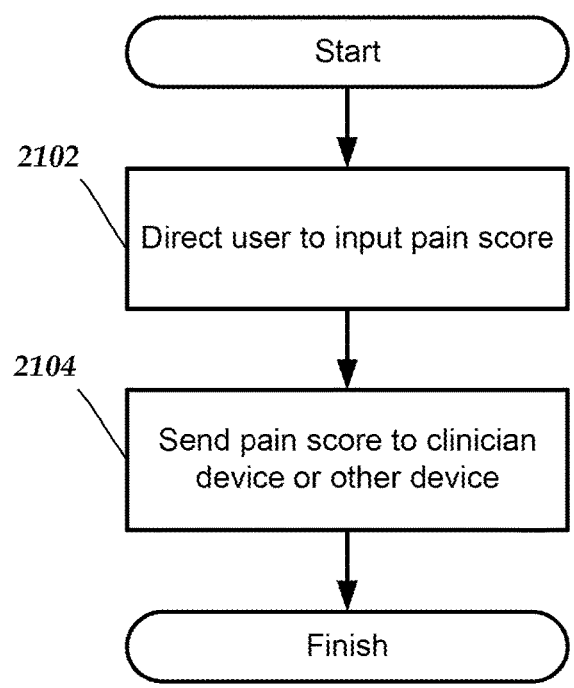
FIG. 21 is a flowchart of one embodiment of a method of inputting a pain score; according to the invention.

FIG. 21 illustrates one embodiment of a method of inputting a pain score. In step 2102, the patient device directs the user to input a pain score and the device receives the pain score. In step 2104, the pain score is sent to the clinician device or other device.

The patient device, user interface, or application may include controls to add friends, create a friend network, send messages to friends, send progress updates or other exercise information to friends or others, or the like. Some of the friends may be other patients, and the patient device, user interface, or application may display comparisons of progress with friends, allow issuance of a challenge to a friend, provide a control to send encouragement to a friend, or other social controls or interaction capabilities. In addition, another application may be available to family, friends, and associates of the patient. This application may allow the user to send encouragement or messages to the patient and may also display progress updates or other exercise information that the patient has permitted. These applications and features can be helpful in encouraging the patient to continue their commitment to the physical therapy or rehabilitation goals and objectives.

Figure 23:
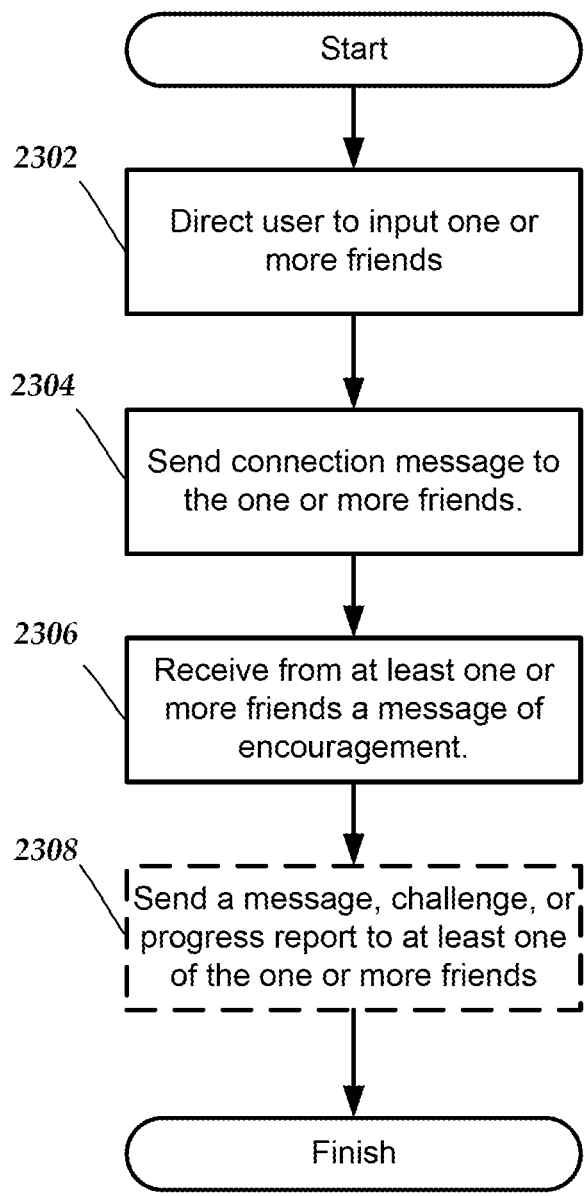
FIG. 23 is a flowchart of one embodiment of a method for including friends in physical therapy; according to the invention.

FIG. 23 illustrates one embodiment of a method for including friends in the physical therapy. In step 2302, the patient is directed to enter one or more friends into the patient device. In step 2304, a connection message is sent to the one or more friends to connect them to the patient's friend network. In step 2306, the patient receives a message of encouragement from at least one of the one or more friends. In optional step 2308, the patient sends a message, challenge, or progress report to at least one of the one or more friends. The progress report can include, for example, an indication of progress by the patient toward at least one physical therapy goal, an indication of performance of the at least one physical therapy exercise by the patient, or an indication of performance of the at least one physical therapy exercise by at least one of the one or more friends, or the like or any combination thereof.

Figure 17:
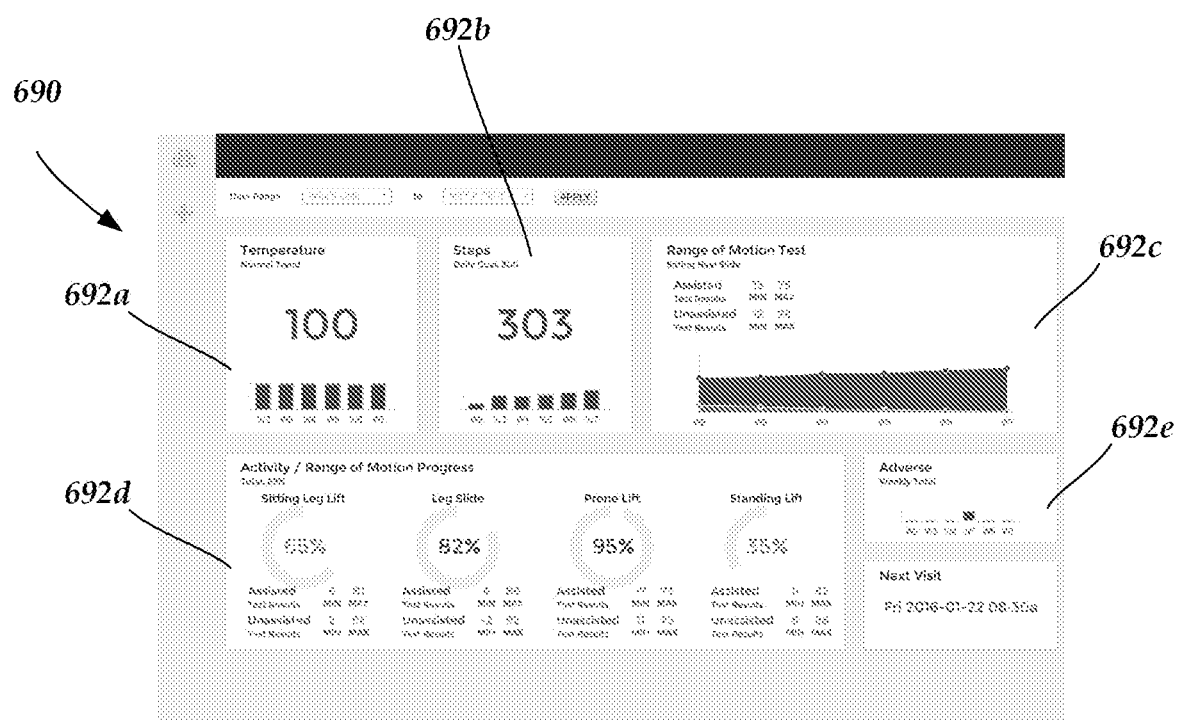
FIG. 17 is a diagram of another embodiment of a user interface to display information obtained from a sensor unit, according to the invention.

FIG. 17 illustrates a user interface 690 that may be suitable for a computer or web interface. The illustrated user interface includes a region 692 displaying the results of temperature measurements 692*a*, step measurements 692*b*, range of motion tests 692*c*, specific exercises and tests 692*d*, and adverse events 692*e*. These results may include numerical information and graphical information. These results may also illustrate graphically or numerically the degree of success in performing exercises (see, for example, region 692*d*) and may also illustrate the degree of compliance with rehabilitation activities (such as the number of exercise repetitions performed). Such an arrangement of information can facilitate monitoring or patient progress, identification of progress or lack of progress, identification of concerns (such as elevated temperature or elevated number of shocks or impacts), and the like.

Other information that can be displayed in one or more pages on the user interface can be include any suitable patient rehabilitation progress data include baselines and progress over time. For example, the information can include baseline range of motion information for exercises such as a sitting leg lift, heel slide, standing lift, prone lift, or the like. The information may also include current range of motion information for these exercises. The information may also include step analysis information including, but not limited to, pre-operation and post-operation average cadence, maximum cadence, stride angle, as well as time spent walking, biking, running, or in sedentary activities. Additional information can include skin temperature, ambient temperature, and trends in temperature. The user interface may also provide information about how many times or how often the patient falls or other notable events. The user interface may provide information from GPS readings from the wearable device or patient device to assess baseline activity, current activity, general activity after surgery or physical therapy or the like.

The user interface of a clinician device may also be used to conduct in-office range of motion tests. The clinician device or patient device may be used to create video of range of motion exercises.

Figure 18:
FIG. 18 is a diagram of a further embodiment of a user interface to display information obtained from a sensor unit, according to the invention.

FIG. 18 illustrates a user interface 790 for a clinician to monitor multiple patients. The region 792 includes information such as patient name, surgery date, sensor date and results of tests 792*a*, number of adverse events, location of the orthopedic implant, and the like. The clinician may also track number of surgeries 794, rate of successful rehabilitation 796, and other suitable information such as, for example, total number of surgeries (for example, total number of knee replacements), average time to reach a particular rehabilitation outcome (for example, average time to reach specified range of motion), and the like.

Figure 19:
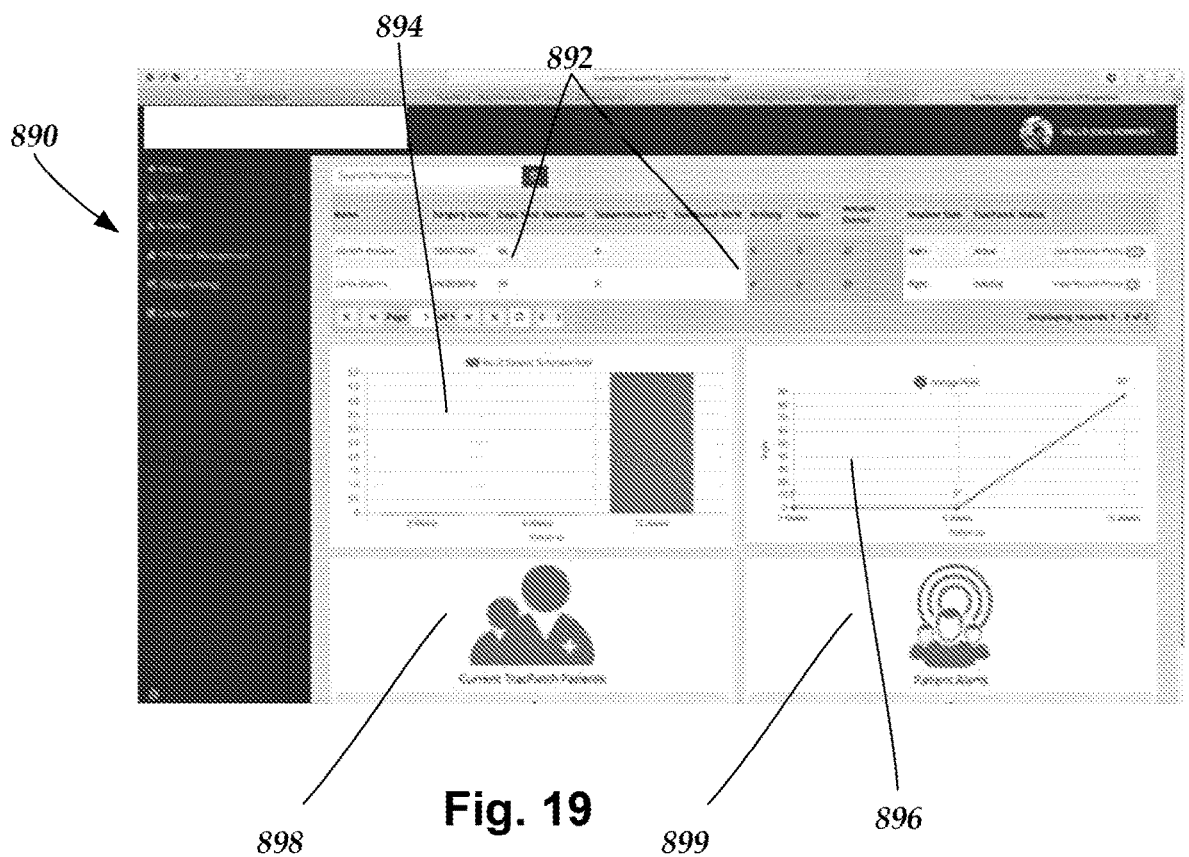
FIG. 19 is a diagram of yet another embodiment of a user interface to display information obtained from a sensor unit, according to the invention.

FIG. 19 illustrates another user interface for a clinician to monitor patients. The region 1592 includes information such as patient name, gender, surgery date, days post operation, measured or trending temperature, range of motion measure, activity, number of steps, notable events, implant site, wearable device status, and the like. The clinician may also track number of successful rehabilitations 894, range of motion achieved over time for a group of patients 896, and other suitable information. Controls may also be provided to access individual patient records 898 or access patient alerts 899.

In at least some embodiments, the applications or user interfaces described herein can be web or application interfaces that are accessible when the patient device or clinician device accesses a server for a content provider. In at least some embodiments, the server or other servers or memory storage devices can store information for the web interface and may also store patient-specific information including patient identification data, sensor data or information derived from sensor data, patient or clinician comments or the like, or any other suitable data. In at least some embodiments, the patient-specific information can be accessed from the patient device, clinician device or other device which, in some embodiments, may require providing credentials (e.g., username or password or both) to access the information.

Additional user interfaces and methods of calculating or otherwise determining information relating to the physical therapy, rehabilitation, or status of the patient are described in U.S. patent application Ser. No. 15/422,312 and U.S. patent application Ser. No. 15/422,299, both of which are filed on even date herewith and incorporated herein by reference.

The methods and systems described herein may be embodied in many different forms and should not be construed as limited to the embodiments set forth herein. Accordingly, the methods and systems described herein may take the form of an entirely hardware embodiment, an entirely software embodiment or an embodiment combining software and hardware aspects. Systems referenced herein typically include memory and typically include methods for communication with other devices including mobile devices. Methods of communication can include both wired and wireless (e.g., RF, optical, or infrared) communications methods and such methods provide another type of computer readable media; namely communication media. Wired communication can include communication over a twisted pair, coaxial cable, fiber optics, wave guides, or the like, or any combination thereof. Wireless communication can include RF, infrared, acoustic, near field communication, Bluetooth™, or the like, or any combination thereof.

It will be understood that each block of the flowchart illustrations, and combinations of blocks in the flowchart illustrations and methods disclosed herein, can be implemented by computer program instructions. These program instructions may be provided to a processor to produce a machine, such that the instructions, which execute on the processor, create means for implementing the actions specified in the flowchart block or blocks disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computer system. In addition, one or more processes may also be performed concurrently with other processes, or even in a different sequence than illustrated without departing from the scope or spirit of the invention.

The computer program instructions can be stored on any suitable computer-readable medium including, but not limited to, RAM, ROM, EEPROM, flash memory or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computer.

The above specification provides a description of the manufacture and use of the invention. Since many embodiments of the invention can be made without departing from the spirit and scope of the invention, the invention also resides in the claims hereinafter appended.

What is claimed as new and desired to be protected by Letters Patent of the United States is:

1. A system for monitoring physical therapy of a patient, the system comprising:
    a patient device configured and arranged for communication with a sensor unit disposed on or within the patient, the patient device comprising a display, a memory, and a processor coupled to the display, and memory, wherein the processor is configured and arranged for performing actions comprising:
        receiving a selection by a user of a one of at least one physical therapy exercise;
        displaying, on the display, a graphical representation of the one of the at least one physical therapy exercise and a user control which, when actuated by the user, indicates that the user is performing the one of the at least one physical therapy exercise;
        upon actuation of the user control, monitoring sensor data from the sensor unit to monitor performance of the one of the at least one physical therapy exercise;
        during performance of the one of the at least one physical therapy exercise, displaying a degree of compliance with the performance of the one of the at least one physical therapy exercise;
        directing, on the display, the user to input one or more friends;
        sending a connection message to each of the one or more friends;
        in response to a patient request, sending a progress report to at least one of the one or more friends, wherein the progress report comprises at least one of a) an indication of progress by the patient toward at least one physical therapy goal or b) an indication of patient performance of at least the one of the at least one physical therapy exercise; and
        receiving, from at least one of the one or more friends, and presenting to the patient a message encouraging the patient to continue physical therapy.

2. The system of claim 1, wherein the actions further comprise
    receiving from the user a request for a range of motion report for a range of motion measurement; and
    displaying, on the display, a graph of a plurality of values for the range of motion measurement obtained over a period of time.

3. The system of claim 2, wherein the actions further comprise
    including the range of motion report in the progress report.

4. The system of claim 2, wherein the actions further comprise
    displaying, on the display, a representation of a pathway to a goal for the range of motion measurement with an indication of current progress of the patient toward that goal.

5. The system of claim 2, wherein the range of motion measurement comprises a range of motion measurement obtained from at least one exercise selected from sitting leg lift, heel slide, standing lift, or prone lift.

6. The system of claim 2, wherein the range of motion measurement comprises a range of motion measurement obtained from a plurality of exercises selected from sitting leg lift, heel slide, standing lift, or prone lift.

7. The system of claim 1, wherein the progress report comprises the indication of patient performance of the one of the at least one physical therapy exercise.

8. The system of claim 7, wherein the progress report further comprises an indication of performance of the at least one physical therapy exercise by at least one of the one or more friends.

9. The system of claim 1, wherein the actions further comprise
    receiving from the user a request for a step analysis; and
    displaying, on the display, step analysis information comprising at least one of pre-operation average cadence, post-operation average cadence, maximum cadence, stride angle, time spent walking, time spent biking, time spent running, or time spent in sedentary activities.

10. The system of claim 9, wherein the actions further comprise
    including the step analysis information in the progress report.

11. The system of claim 1, wherein the actions further comprise
    receiving from the user a request for an exercise summary; and
    displaying, on the display, a summary of a plurality of physical therapy exercises indicating a number of repetitions performed for each of the physical therapy exercises over a period of time.

12. The system of claim 11, wherein the actions further comprise
    including the exercise summary in the progress report.

13. The system of claim 1, wherein the actions further include
    directing, on the display, a user to take a photograph or video of a site on the patient;
    upon receiving a user-input to take the photograph or video, taking the photograph or video; and
    storing the photograph or video in memory.

14. The system of claim 13, wherein the actions further include performing a pigment analysis using the photograph or video to assess health of the site on the patient, possible infection, or inflammation.

15. The system of claim 1, wherein the actions further include
    in response to user input, sending a message to at least one of the one or more friends.

16. The system of claim 1, wherein the actions further include
    in response to user input, sending a challenge to at least one of the one or more friends.

17. The system of claim 1, wherein the progress report comprises the indication of progress by the patient toward the at least one physical therapy goal.

18. The system of claim 1, wherein the actions further comprise
- directing, on the display, a user to input a pain score; and
- sending the pain score to a clinician device.

19. The system of claim 1, wherein the actions further comprise
- during performance of the one of the at least one physical therapy exercise, displaying a count of repetitions of the one of the at least one physical therapy exercise being performed.

20. The system of claim 1, wherein the actions further comprise
- during performance of the one of the at least one physical therapy exercise, displaying either a current value or a maximum achieved value of a range of motion measurement associated with the one of the at least one physical therapy exercise, as determined from the sensor data.

* * * * *